US008426398B2

(12) United States Patent
Joshi et al.

(10) Patent No.: US 8,426,398 B2
(45) Date of Patent: Apr. 23, 2013

(54) CONJUGATES OF NOSCAPINE AND FOLIC ACID AND THEIR USE IN TREATING CANCER

(75) Inventors: Harish C. Joshi, Decatur, GA (US); Surya N. Vangapandu, Alpharetta, GA (US); Ritu Aneja, Lilburn, GA (US)

(73) Assignee: Emory University, Atlanta, GA (US)

( * ) Notice: Subject to any disclaimer, the term of this patent is extended or adjusted under 35 U.S.C. 154(b) by 77 days.

(21) Appl. No.: 13/142,908

(22) PCT Filed: Jan. 8, 2010

(86) PCT No.: PCT/US2010/020472
§ 371 (c)(1),
(2), (4) Date: Aug. 10, 2011

(87) PCT Pub. No.: WO2010/083104
PCT Pub. Date: Jul. 22, 2010

(65) Prior Publication Data
US 2011/0286919 A1 Nov. 24, 2011

Related U.S. Application Data

(60) Provisional application No. 61/144,328, filed on Jan. 13, 2009.

(51) Int. Cl.
*A01N 43/00* (2006.01)
*A01N 43/42* (2006.01)
*A61K 31/33* (2006.01)
*C07D 475/00* (2006.01)

(52) U.S. Cl.
USPC ............................. 514/183; 514/291; 544/261

(58) Field of Classification Search .................. None
See application file for complete search history.

(56) References Cited

U.S. PATENT DOCUMENTS

| 4,922,901 A | 5/1990 | Brooks et al. |
| 5,140,104 A | 8/1992 | Coughlin et al. |
| 7,128,893 B2 | 10/2006 | Leamon et al. |

FOREIGN PATENT DOCUMENTS

| KR | 1020080104928 | 12/2008 |
| WO | 2005081711 | 9/2005 |
| WO | 2007122829 | 1/2007 |

OTHER PUBLICATIONS

Bartlett et al., (2007), "Physicochemical and Biological Characterization of Targeted, Nucleic Acid-Containing Nanoparticles.", Bioconjugate Chemistry, 18(2): 456-468.
Bettio et al., (2006), "Synthesis and Preclinical Evaluation of a Folic Acid Derivative Labeled with 18F for PET Imaging of Folate Receptor—Positive Tumors.", Journal of Nuclear Medicine, 47(7): 1153-1160.
Blanke, C., (2002), "Celecoxib with chemotherapy in colorectal cancer.", Oncology (Williston Park), 16(4 Suppl 3): 17-21.
Gravier et al., (2008), "Improvement of meta-tetra(Hydroxyphenyl)chlorin-Like Photosensitizer Selectivity with Folate-Based Targeted Delivery. Synthesis and in Vivo Delivery Studies.", Journal of Medicinal Chemistry, 51(13): 3867-3877.
Landen et al., (2002), "Noscapine Alters Microtubule Dynamics in Living Cells and Inhibits the Progression of Melanoma.", Cancer Res, 62(14): 4109-4114.
Naik, et al., In silico inspired design and synthesis of a novel tubulin-binding anti-cancer drug: folate conjugated noscapine (Targetin). J Comput Aided Mol Des (2012) 26:233-247.
Kyprianou et al., (2000), "Suppression of Human Prostate Cancer Cell Growth by α1-Adrenoceptor Antagonists Doxazosin and Terazosin via Induction of Apoptosis.", Cancer Res, 60(16): 4550-4555.
Adjei et al., (2001), "Synergy of the Protein Farnesyltransferase Inhibitor SCH66336 and Cisplatin in Human Cancer Cell Lines.", Clinical Cancer Research, 7(5): 1438-1445.
Giermasz et al., (2002), "Potentiating antitumor effects of a combination therapy with lovastatin and butyrate in the Lewis lung carcinoma model in mice.", International Journal of Cancer, 97(6): 746-750.
Landen et al., (2004), "Noscapine Crosses the Blood-Brain Barrier and Inhibits Glioblastoma Growth.", Clinical Cancer Research, 10(15): 5187-5201.
Westerhof et al., (1991), "Membrane Transport of Natural Folates and Antifolate Compounds in Murine L1210 Leukemia Cells: Role of Carrier- and Receptor-mediated Transport Systems.", Cancer Res, 51(20): 5507-5513.
Zhou et al., (2003), "Brominated Derivatives of Noscapine Are Potent Microtubule-interfering Agents That Perturb Mitosis and Inhibit Cell Proliferation.", Molecular Pharmacology, 63(4): 799-807.
Zhou et al., (2002), "Paclitaxel-resistant Human Ovarian Cancer Cells Undergo c-Jun NH2-terminal Kinase-mediated Apoptosis in Response to Noscapine.", Journal of Biological Chemistry, 277(42): 39777-39785.
Zhou et al., (2005), "Targeting Microtubules for Cancer Chemotherapy.", Current Medicinal Chemistry—Anti-Cancer Agents, 5(1): 65-71.
Zhou et al., (2002), "Minor Alteration of Microtubule Dynamics Causes Loss of Tension across Kinetochore Pairs and Activates the Spindle Checkpoint.", Journal of Biological Chemistry, 277(19): 17200-17208.
Zou et al., (1998), "Combined effect of chemopreventive agent N-(4-hydroxyphenyl) retinamide (4-HPR) and gamma-radiation on bladder cancer cell lines.", Int J Oncol, 13(5): 1037-1041.

*Primary Examiner* — Craig Ricci
*Assistant Examiner* — Jared D Barsky
(74) *Attorney, Agent, or Firm* — Emory Patent Group; James C. Mason; Susanne Hollinger

(57) ABSTRACT

The present invention is directed to compounds which are conjugates of two non-toxic natural products, noscapine (and various noscapine analogs) and folic acid (and various folic acid analogs), where the folic acid is conjugated to noscapine or the noscapine analog at the 9-position on the isoquinoline ring on the noscapine framework. Pharmaceutical compositions including the compounds, and methods of treating various tumors using the compounds and compositions, are also disclosed. The conjugates are particularly useful for treating cancers which overexpress the Folate Receptor α (FRα) receptor.

9 Claims, 9 Drawing Sheets

Colchicine

MTC

Podophyllotoxin

Noscapine

CONJUGATES OF NOSCAPINE AND FOLIC ACID AND THEIR USE IN TREATING CANCER

This invention was made with government support under Grant No. 1 R01 CA095317-01A2, awarded by the National Institutes of Health. The government has certain rights in the invention.

FIELD OF THE INVENTION

The present invention relates to novel methods and compositions for treating primary and metastatic cancers and other proliferative disorders. These methods and compositions use conjugates of noscapine or noscapine analogs with folic acid or folic acid analogs. These compounds, and pharmaceutical compositions including the compounds, are particularly useful for treating primary and metastatic cancers in humans. The invention also encompasses the varying modes of administration of the therapeutic compounds or compositions. The compounds can also be radiolabeled and used in non-invasive diagnostic/prognostic imaging tools for FR-alpha positive cancers.

BACKGROUND OF THE INVENTION

Right behind cardiovascular problems (such as heart attacks), cancer is the most common cause of death in the United States. Although there has been significant success in the preventive, palliative and treatment strategies for cardiovascular disorders, many cancer types still go undiagnosed until a late stage (metastasis away from the site of origin). This is primarily because routine clinical check-ups do not reveal them in early stages (for example, ovarian and brain cancers). Additionally, prostate and breast cancers, although often can be diagnosed before terminal stages, the recurrence of new tumors that evade the primary modality of treatment (surgery, radiation, hormone- and chemo-therapy) emerge often at different metastatic sites often the bone and lungs.

Noscapine, and various noscapine analogs, are known to exhibit tubulin-binding properties, without substantially altering tubulin polymerization, and have been shown in the clinic to be useful anti-cancer agents. Noscapine is currently in clinical trials.

Folic acid receptors (FR-α receptors) are overexpressed in many tumor types, particularly in cancers of ovary, breast, prostate, and brain (gliomas and pituitary adenomas).

To date, there have been no modifications of the noscapine framework which target the noscapine to tumor cells. It would be advantageous to provide noscapine analogs which effectively target tumor cells. The present invention provides such noscapine analogs.

SUMMARY OF THE INVENTION

The present invention is directed to compounds which are conjugates of two non-toxic natural products, noscapine and folic acid, as well as various non-natural noscapine and folic acid analogs. Pharmaceutical compositions including the compounds, and methods of treating various tumors using the compounds and compositions, are also disclosed.

The compounds comprise a noscapine or noscapine analog linked, at the 9-position of noscapine, to folic acid or a folic acid derivative. The linkage can be an amide linkage, thioamide linkage, ester linkage, thioester linkage, carbamate linkage, thiocarbamate linkage, urea linkage, or thiourea linkage. An amide linkage is preferred.

Noscapine and various noscapine analogs are known to inhibit tubulin binding, and folic acid (and its analogs) are known to target anticancer drugs in high concentrations to tumors. The conjugate, therefore, can target the tumors, and treat or prevent a subset of these tumors that often overexpress a receptor for folic acid (vitamin-B9, required for aggressive tumor growth).

The anti-cancer properties of noscapine have been extensively studied, and noscapine is now in a Phase I/II clinical trial. The noscapine/folic acid conjugate (herein referred to as "Targetin") shows enhanced antitumor efficacy relative to noscapine. Because folic acid and noscapine are each non-toxic, and the conjugate additionally appears to be non-toxic, it is believed that treatment of various cancer types which over-express a receptor for folic acid can extend the disease-free survival of cancer patients without compromising their quality of life. In one embodiment, the treatment can not only prevent the recurrence of tumors, it can be used to treat surgically un-removable, dispersed tumor foci.

Methods for diagnosing whether a particular tumor type will respond to treatment with the compounds described herein, for example, using imaging studies (which themselves will use labeled Targetin analogs) are also disclosed.

μM (◄), 75 μM (►) and 100 μM (♦) Panel B, double-reciprocal plot for Targetin binding to tubulin. Panel C, the effects of noscapine and Targetin on assembly of tubulin into microtubules in vitro. Equivalent amount of solvent DMSO was used as a negative control. Control (■), 25 μM noscapine (●), 100 μM noscapine (▲) (symbols are overlapping), 25 μM Targetin (▼) and 100 μM Targetin (◄).

Figure 6:
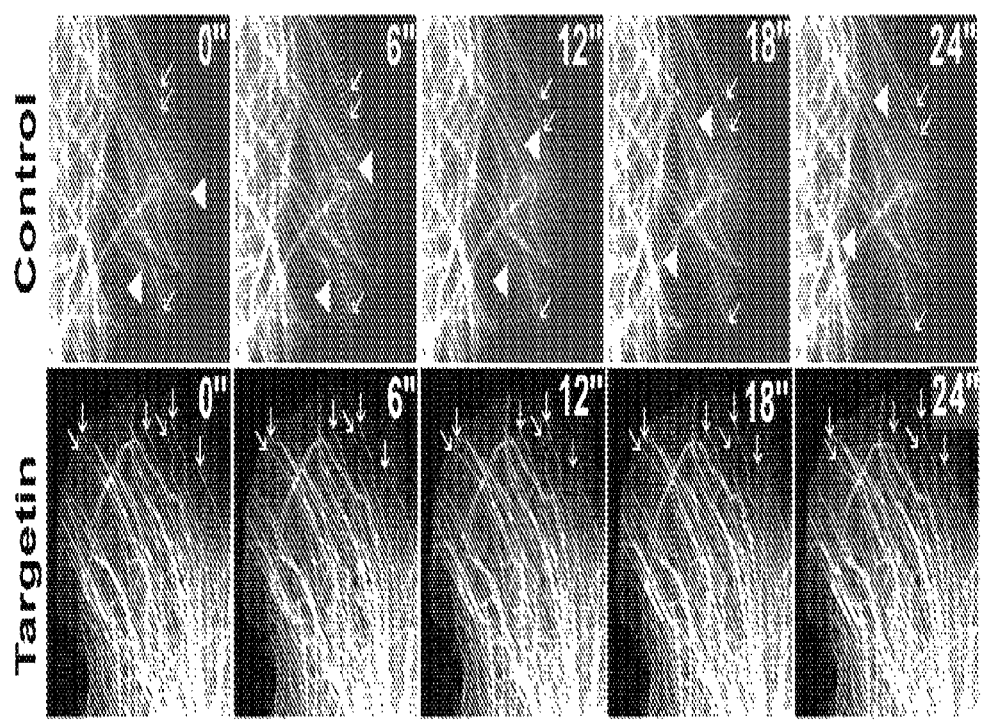

FIG. 6 is a series of photographs showing how Targetin increases the pause-time of cellular MTs. A gallery of video frames, 6 seconds apart, of plus ends of several microtubules in control and Targetin treated cells. As can be seen by the arrows in the Targetin treated cells, the positions of microtubule ends do not change over 24 seconds.

Figure 7:
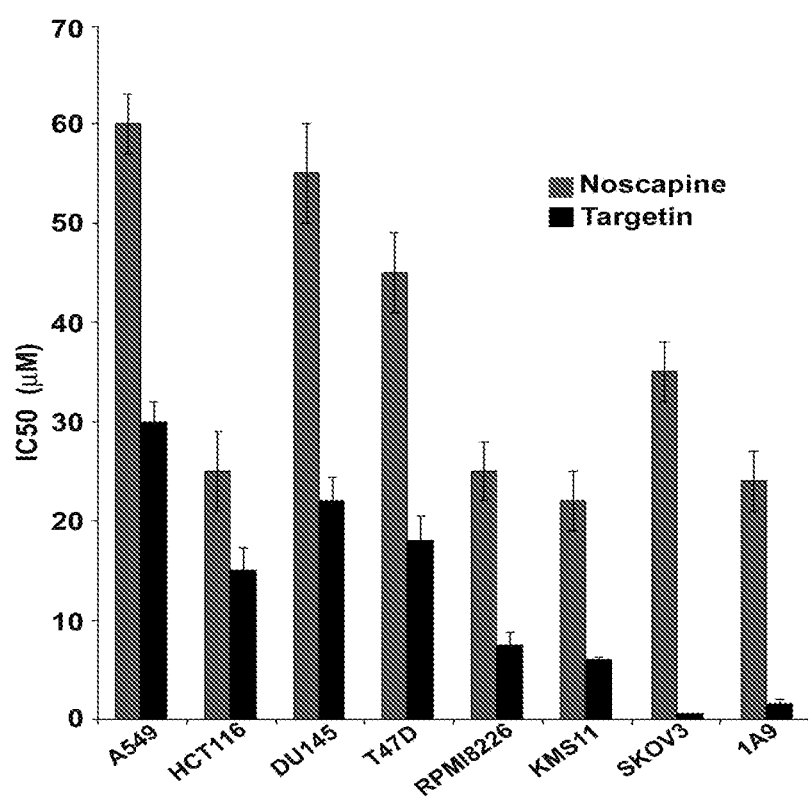

FIG. 7 is a chart showing the $IC_{50}$ (a drug concentration required to achieve a 50% inhibition of cellular proliferation) of noscapine and Targetin for various cancer cell types distinct in their folate receptor expression status.

Figure 8:
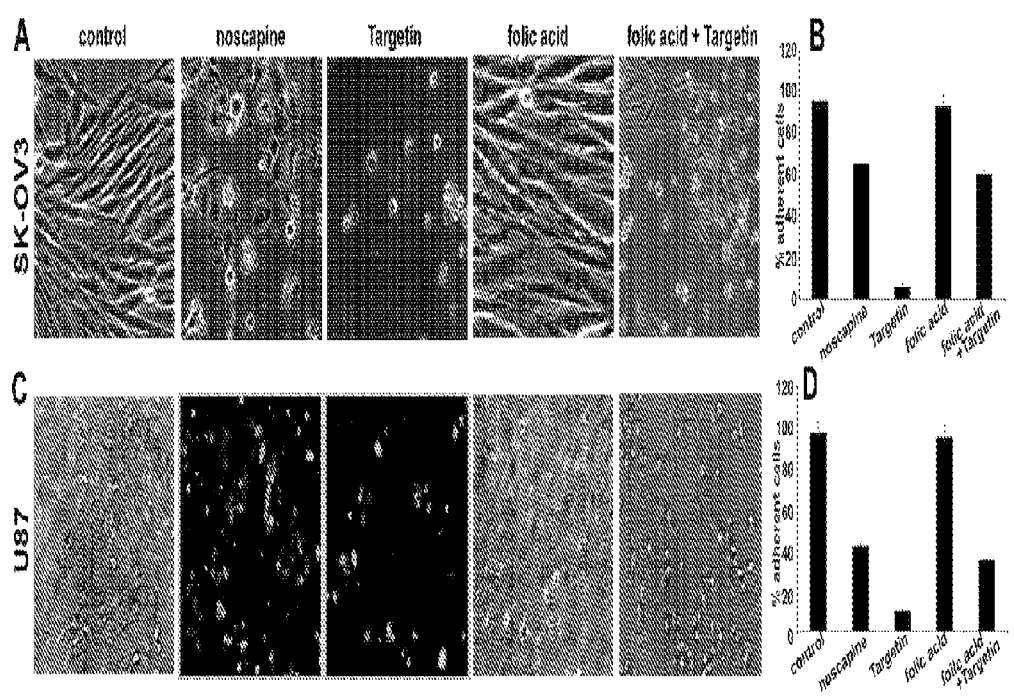

FIG. 8 are phase contrast images of human SKOV3 ovarian cancer cells (A), and human U87 brain glioplastoma cells (C) treated for 48 hours with vehicle solution (DMSO), noscapine, Targetin, folic acid, and folic acid+Targetin. Live cells remain adherent and exclude Trypan blue (although a few late stage dying cells that remain adherent are Trypan blue-positive, and are not counted as live adherent). The numbers of adherent live cells are quantified in panels B and D respectively.

DETAILED DESCRIPTION

Compounds, pharmaceutical compositions including the compounds, and methods of preparation and use thereof are disclosed. The compounds are conjugates of noscapine or noscapine analogs and folic acid or folic acid analogs.

The following definitions will be useful in understanding the metes and bounds of the invention as described herein.

As used herein, "alkyl" refers to straight chain or branched alkyl radicals including $C_1$-$C_8$, preferably $C_1$-$C_5$, such as methyl, ethyl, or isopropyl; "substituted alkyl" refers to alkyl radicals further bearing one or more substituent groups such as hydroxy, alkoxy, aryloxy, mercapto, aryl, heterocyclo, halo, amino, carboxyl, carbamyl, cyano, and the like; "alkenyl" refers to straight chain or branched hydrocarbon radicals including $C_1$-$C_8$, preferably $C_1$-$C_5$ and having at least one carbon-carbon double bond; "substituted alkenyl" refers to alkenyl radicals further bearing one or more substituent groups as defined above; "cycloalkyl" refers to saturated or unsaturated, non-aromatic, cyclic ring-containing radicals containing three to eight carbon atoms, preferably three to six carbon atoms; "substituted cycloalkyl" refers to cycloalkyl radicals further bearing one or more substituent groups as defined above; "aryl" refers to aromatic radicals having six to ten carbon atoms; "substituted aryl" refers to aryl radicals further bearing one or more substituent groups as defined above; "alkylaryl" refers to alkyl-substituted aryl radicals; "substituted alkylaryl" refers to alkylaryl radicals further bearing one or more substituent groups as defined above; "arylalkyl" refers to aryl-substituted alkyl radicals; "substituted arylalkyl" refers to arylalkyl radicals further bearing one or more substituent groups as defined above; "heterocyclyl" refers to saturated or unsaturated cyclic radicals containing one or more heteroatoms (e.g., O, N, S) as part of the ring structure and having two to seven carbon atoms in the ring; "substituted heterocyclyl" refers to heterocyclyl radicals further bearing one or more substituent groups as defined above.

I. Compounds

The compounds are conjugates of noscapine or noscapine analogs, with folic acid or folic acid analogs. The folic acid or folic acid analog is conjugated to the noscapine or noscapine analog at the 9-position of the isoquinoline ring in the noscapine framework. The position at which the folic acid or folic acid analog is linked to the noscapine analog can be through either of the carboxylic acid moieties in folic acid, or through an amine group.

The compounds generally have one of the following formulas:

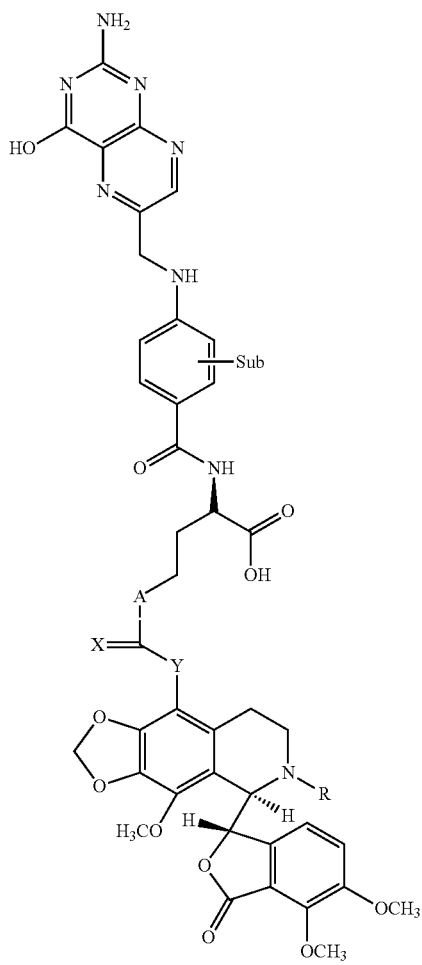

Formula 1 wherein:

R is H, $C_{1-6}$ alkyl, $C_{1-6}$ substituted alkyl, aryl, substituted aryl, arylalkyl, substituted arylalkyl, alkaryl, substituted alkaryl, heteroaralkyl, substituted heteroaralkyl, heterocyclyl, and substituted heterocyclyl, R also includes the substituents at the $R_1$ position of the noscapine analogs described in PCT WO 2007/133112 A1, the contents of which are hereby incorporated by reference;

the term "substituted" as applied to alkyl, aryl, cycloalkyl and the like refers to the substituents selected from the group consisting of hydroxy, alkoxy, aryloxy, mercapto, aryl, heterocyclo, halo, amino, carboxyl, carbamyl, and cyano.

"Sub" refers to one to three substituents at any position on the aryl ring, wherein the substituents are the substituents described above, A is O, S, NR, or a covalent linkage, X is O, S, or NR, and Y is O, S, or NR;

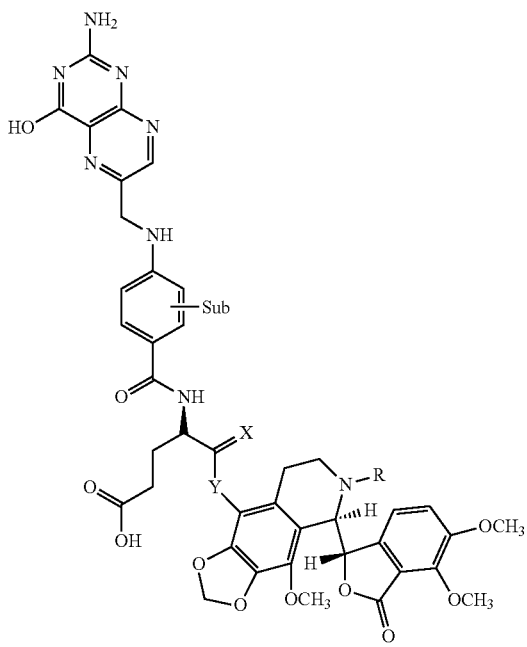

Wherein X, Y, R, and Sub are as described above with respect to Formula 1,

Formula 3

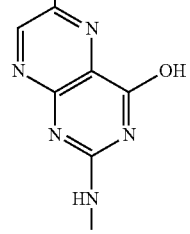

Formula 2

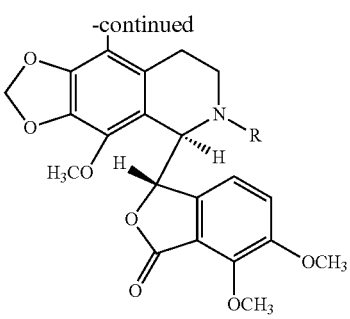

wherein R and Sub are as defined above with respect to Formula 1, and

Formula 4

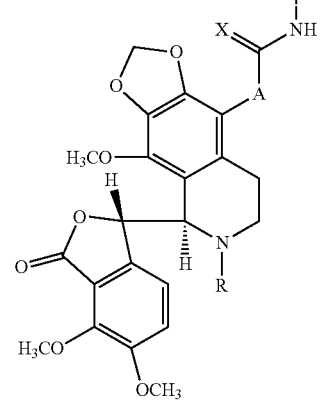

Wherein:

A, R, Sub, and X are as defined above with respect to Formula 1.

The compounds can be prepared, for example, by reacting a functional group at the 9-position on the noscapine or noscapine analog with a functional group on the folic acid, optionally using a conjugating agent to facilitate the coupling chemistry, and optionally protecting and deprotecting those functional groups not involved in the coupling chemistry, for example, using protecting groups described in Greene and Wuts, Protective Groups in Organic Synthesis, Third Edition, Wiley Interscience (1999).

The carboxylic acid group on the folic acid can be a carboxylic acid, a thiocarboxylic acid, or an activated analog thereof, such as an anhydride, acid halide, and the like. Conjugating agents are well known to those of skill in the art, and include dicyclohexyl diimide (DCI), and the like. The conjugation can occur in a stepwise manner, or in one step, depending on the linkage between the folic acid analog and the noscapine analog.

In one embodiment, rather than being conjugated to the folic acid or folic acid analogs described herein, the 9-position of the noscapine or noscapine analog can be linked to one or more small targeting peptide ligands, antibodies, or nucleic acid aptamers, which are selective for FR-alpha or other cancer types.

Noscapine and Noscapine Analogs

The compounds are conjugates of noscapine or noscapine analogs, which generally fall within the formula provided below, with folic acid or folic acid analogs:

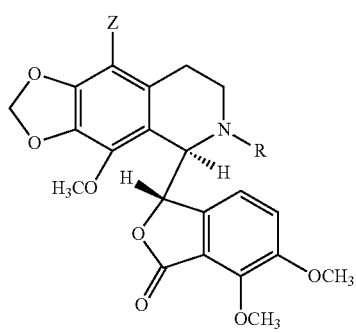

Formula I wherein Z is a moiety capable of linking the noscapine or noscapine analog, at its 9-position, to the folic acid or folic acid analog.

Before the noscapine is conjugated, Z can be, for example, halo, amino, thio, hydroxy, carboxylic acid, and thiocarboxylic acid.

R is H, $C_{1-6}$ alkyl, $C_{1-6}$ substituted alkyl, aryl, substituted aryl, arylalkyl, substituted arylalkyl, alkaryl, substituted alkaryl, heteroaralkyl, substituted heteroaralkyl, heterocyclyl, and substituted heterocyclyl, and R also includes the substituents at the $R_1$ position of the noscapine analogs described in PCT WO 2007/133112 A1, the contents of which are hereby incorporated by reference;

the term "substituted" as applied to alkyl, aryl, cycloalkyl and the like refers to the substituents described above.

The compounds can be prepared, for example, by performing electrophilic aromatic substitution on the isoquinoline ring of noscapine (the compounds described above, where X is H and R is methyl), or a noscapine analog, where R is other than methyl), typically under conditions that do not result in significant hydrolysis of the noscapine framework.

The conjugation to the folic acid or folic acid analog typically is at the 9-position on the isoquinoline ring. This means that a functional group, capable of conjugating with the folic acid or folic acid analog must be present at the 9-position. Functional groups useful for this conjugation include, for example, halo, amine, thio, hydroxy, and carboxy groups.

The halogenation of noscapine can be performed using various procedures, depending on the particular halogen, as summarized below in Scheme 1.

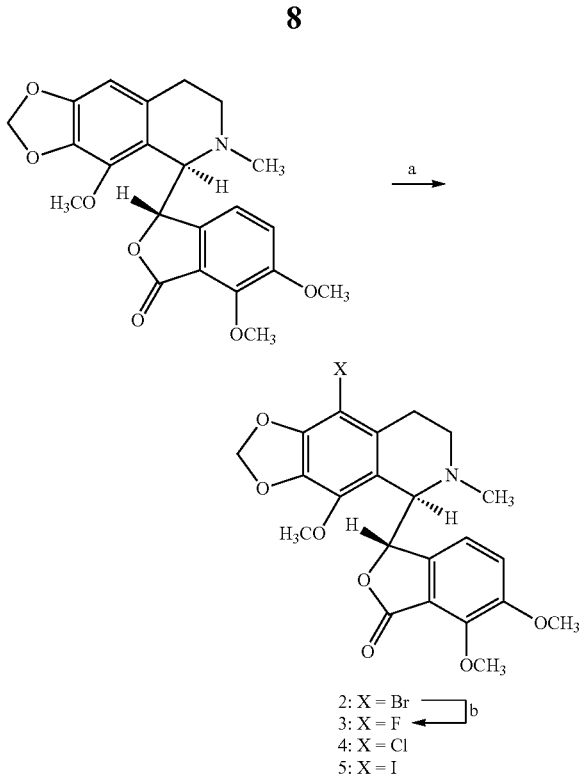

2: X = Br
3: X = F
4: X = Cl
5: X = I

Semi-synthetic derivatives of noscapine, Reagents and reaction conditions-a) compound 2: $Br_2$—$H_2O$; 48% HBr, 82%; Compound 4: $SO_2Cl_2$, $CHCl_3$, 90%; Compound 5: Pyr-ICl, $CH_3CN$, 71%. b) $F_2$, Amberlyst-A, THF, 74%

Noscapine can be brominated at the 9-position by reacting noscapine with concentrated hydrobromic acid. Noscapine can be fluorinated using the fluoride form of Amberlyst-A 26, or by Br/F exchange. Iodination of noscapine typically required low-acid conditions. One successful approach for preparing 9-I-nos involved treating a solution of noscapine in acetonitrile with pyridine-iodine chloride at room temperature for 6 hours followed by raising the temperature to 100° C. for another 6 hours.

9-Chloro-Nos can be prepared by performing electrophilic aromatic substitution on the isoquinoline ring of noscapine, typically under conditions that do not result in significant hydrolysis of the noscapine framework. The chloro substituent can be added to the 9-position on the isoquinoline ring using a variety of known aromatic chlorination conditions, one of which is shown below.

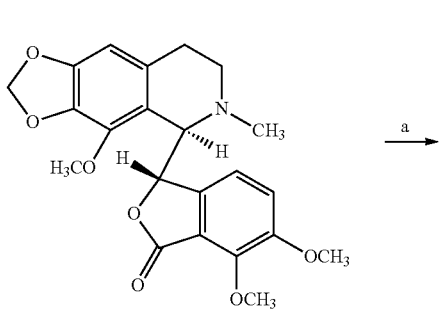

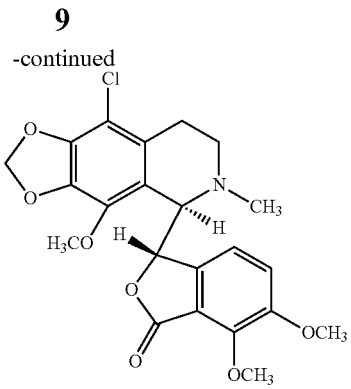

a: SO₂Cl₂, CHCl₃, 90%

Chlorination of noscapine using sulfuryl chloride in chloroform at low temperature provides excellent yields and the desired regioselectivity.

9-Amino-Nos can be prepared, for example, by first performing a nitration reaction on the isoquinoline ring of noscapine, ideally under conditions that do not result in significant hydrolysis of the noscapine framework. The nitro group adds predominantly at the 9-position of noscapine. The nitro group can then be reduced to an amino (NH₂) substituent using conventional techniques. One representative set of nitration conditions involves using stoichiometric silver nitrate and a slight excess of trifluoroacetic anhydride.

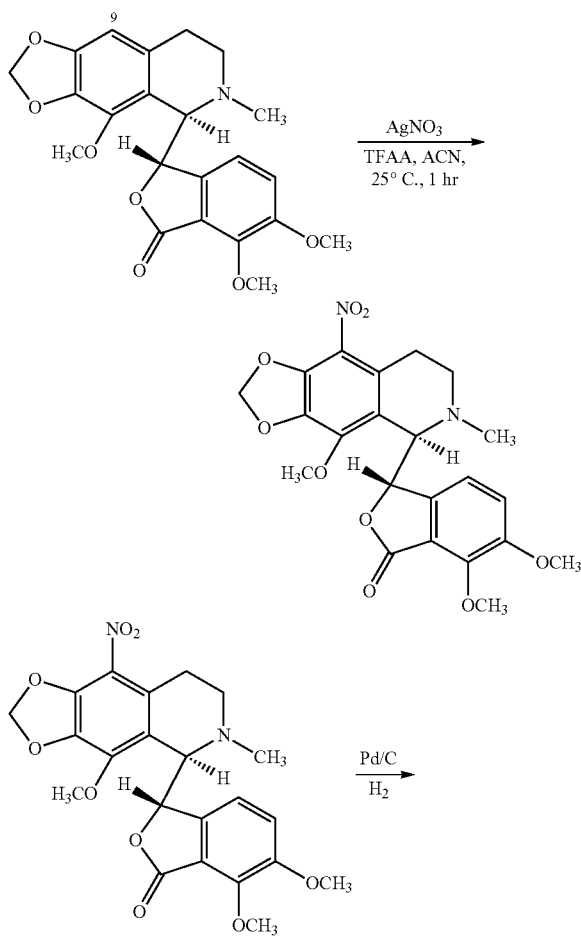

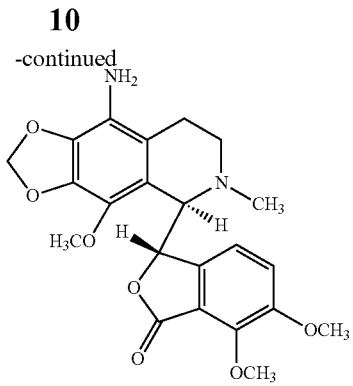

Folic Acid and Folic Acid Analogs
Folic acid has the following formula:

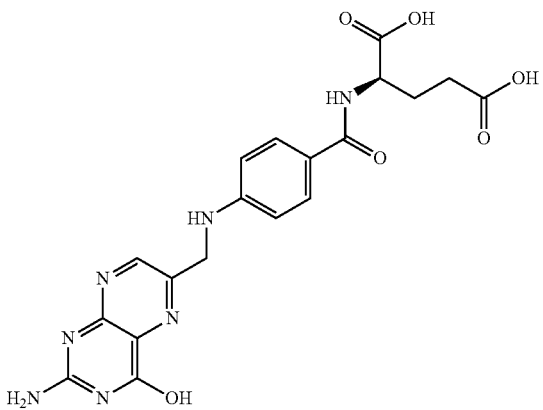 [SMILES: Nc1nc(O)c2nc(CNc3ccc(C(=O)N[C@H](CCC(=O)O)C(=O)O)cc3)cnc2n1]

As used throughout the instant specification the term "folic acid analog" is intended to encompass any analog of folic acid that contains at least one carboxyl group and that binds to the relevant folic acid receptor.

The term "amine derivative of folic acid" is intended to encompass any folic acid analog that contains or has been modified to contain a reactive amine.

The term "reactive amine" is intended to encompass any nitrogen-containing functional group that can be covalently attached or bonded through a nitrogen atom to an aldehyde functional group either by a simple chemical condensation reaction or by a chemical condensation reaction followed by reduction to stabilize the covalent bond formed Examples of such reactive amines include but are not limited to: primary amine, secondary amine, hydrazine, hydrazide, phenylhydrazine, alkoxyamine, semicarbazide and thiosemicarbazide.

Representative folic acid analogs include folinic acid, methotrexate, aminopterin, 3',5'dichloromethotrexate, 3',5'dichloroaminopterin, 5,8-dideazamethotrexate, 5,8-dideaza 5,6,7,8-tetrahydromethotrexate, 5,8-dideaza 5,6,7,8-tetrahydroaminopterin, 5,8,10-trideazaminopterin, 5,10-dideazatetrahydrofolic acid, and 8,10-dideazaminopterin. Other folic acid analogs include those described, for example, in U.S. Pat. No. 5,140,104.

It is known that some folate analogues also bind with high affinity to the FR (reviewed by Westerof, G. R., Jansen, G., van Emmefik, N., Kathmann, I., Rijksen, G., Jackman, A. L. & Schornagel, J. H. et al. [1991] Cancer Research 51, 5507-5513). These include CB3717 ($N_{10}$-propargyl-5,8-dideazafolic acid) and ICI-198,583 (2-deamino-2-methyl-$N_{10}$-propargyl-5,8-dideazafolic acid), which are available from ICI-Pharmaceuticals Division (Aidefly Park, Macclesfield, Chesire, United Kingdom).

Folate analogs which have high affinity for the FR, the reduced folate carrier (RFC) and/or the proton-coupled folate transporter (PCFT) will also be effective for forming conjugates with noscapine, which conjugates are useful for targeting tumor cells that are FR positive. Those analogs which bind to the reduced folate carrier (RFC) or the proton-coupled folate transporter (PCFT) will help internalize the noscapine/folic acid conjugate inside a cancer cell. In one embodiment, the folate analogues have high affinity for the FR, but lower affinity for the reduced folate/MTX carrier.

Conjugates which include a folic acid analog which binds to the reduced folate carrier (RFC) and/or the proton-coupled folate transporter (PCFT) will be both targeted to, and internalized by, the tumor cell.

Amine derivatives of these and other folic acid analogs are useful according to the present invention. Such amine derivatives encompass any folic acid analog containing or modified to contain a reactive amine moiety. The term "reactive amine" is intended to encompass any nitrogen-containing functional group that can be covalently attached or bonded through a nitrogen atom to an aldehyde functional group either by a single chemical condensation reaction or by a chemical condensation reaction followed by reduction to stabilize the covalent bond formed. Thus amine derivatives of folic acid analogs useful according to the invention include but are not limited to: methotrexate-gamma-hydrazide, methotrexate-$\alpha$-hydrazide, 3'5-dichloromethotrexate-gamma-hydrazide, 3',5-dichloromethotrexate-$\alpha$-hydrazide, methotrexate-$\alpha$-$\alpha$-lysylglycyl-glycyl-tyrosyl hydrazide, methotrexate-gamma-tyrosyl hydrazide, methotrexate-$\alpha$-$\alpha$-lysyl hydrazide, methotrexate-$\alpha$-$\alpha$-lysine, methotrexate-$\alpha\alpha$-lysyl-epsilon-arginine-glycine-glycine-tyrosine, aminopterin-gamma-hydrazide, aminopterin-$\alpha$-hydrazide, 3'5'-dichloraminopterin-gamma-hydrazide, 3'5'-dichloroaminopterin-$\alpha$-hydrazide, aminopterin-gamma-tyrosyl hydrazide, aminopterin-$\alpha$-$\alpha$-lysyl-glycyl-tyrosyl hydrazide, aminopterin-$\alpha$-$\alpha$-lysyl hydrazide, aminopterin-$\alpha$-$\alpha$-lysine, and aminopterin-$\alpha$-$\alpha$-lysyl-epsilon-arginine-glycine-glycine-tyrosine. Reactive amine-containing derivatives of folic acid analogs such as 5,8-dideazamethotrexate, 5,8-dideaza 5,6,7,8-tetrahydromethotrexate, 5,8,-dideaza 5,6,7,8-tetrahydroaminopterin, 5,8,10-trideazatetrahydrofolic acid, and 8,10-dideazaminopterin are also useful according to the invention.

Conjugation Chemistry

Acyl conjugate forms can be synthesized by acylation of amino groups on noscapine or noscapine analogs with appropriate acylating agents (i.e., folic acid and folic acid analogs). For example, amides can be prepared by reacting the amine in 9-amino noscapine, or a different noscapine analog with a 9-amino substituent, directly with a carboxylic acid moiety on folic acid or a folic acid analog, using a coupling agent, such as dicyclohexyl carbodiimide (DCC), or by reacting the amine with an activated derivative of the carboxylic acid, such as an acid halide or an acid anhydride. Thioamides can be prepared from amides using Lawesson's reagent. Ureas can be prepared by reacting the amines in the noscapine or noscapine analog with isocyanates on a folic acid analog. Thioureas can be prepared in a similar fashion using isothiocyanates. Carbamates can be formed by reacting the amines with haloformates or other carbonate-like alkoxycarbonyl transfer agents (e.g., di-t-butyl dicarbonate).

In some embodiments, the folic acid analog includes amine groups, which can react with a carboxylic acid group present at the 9-position on noscapine, or can be coupled with an agent, such as methyl chloroformate, phosgene, thiophosgene, and the like, which can react with an amine group at the 9-position of a noscapine analog and an amine group on a folic acid derivative in a stepwise fashion.

An amine-containing folic acid analog can react with a 9-halo-noscapine analog to form an amine linkage.

Though less stable than amides or thioamides, esters or thioesters can be similarly prepared, by using a 9-hydroxy or 9-thio noscapine analog, and reacting that with a carboxylic acid group on folic acid or a carboxy group-containing folic acid analog.

The foregoing chemistry is well known to those in the field of organic synthesis. Representative coupling conditions are described below in the working examples.

II. Pharmaceutical Compositions

The compounds described herein can be incorporated into pharmaceutical compositions and used to prevent a condition or disorder in a subject susceptible to such a condition or disorder, and/or to treat a subject suffering from the condition or disorder. The pharmaceutical compositions described herein include one or more of the conjugates described herein, and/or pharmaceutically acceptable salts thereof. Optically active compounds can be employed as racemic mixtures, as pure enantiomers, or as compounds of varying enantiomeric purity.

The manner in which the compounds are administered can vary. The compositions are preferably administered orally (e.g., in liquid form within a solvent such as an aqueous or non-aqueous liquid, or within a solid carrier). Preferred compositions for oral administration include pills, tablets, capsules, caplets, syrups, and solutions, including hard gelatin capsules and time-release capsules. Compositions may be formulated in unit dose form, or in multiple or subunit doses. Preferred compositions are in liquid or semisolid form. Compositions including a liquid pharmaceutically inert carrier such as water or other pharmaceutically compatible liquids or semisolids may be used. The use of such liquids and semisolids is well known to those of skill in the art.

The compositions can also be administered via injection, i.e., intraveneously, intramuscularly, subcutaneously, intraperitoneally, intraarterially, intrathecally; intravitreally, subconjunctivally, periocularly and intracerebroventricularly. Intravenous administration is a preferred method of injection. Suitable carriers for injection are well known to those of skill in the art, and include 5% dextrose solutions, saline, and phosphate buffered saline. The compounds can also be administered as an infusion or injection (e.g., as a suspension or as an emulsion in a pharmaceutically acceptable liquid or mixture of liquids).

The formulations may also be administered using other means, for example, rectal administration. Formulations useful for rectal administration, such as suppositories, are well known to those of skill in the art. The compounds can also be administered by inhalation (e.g., in the form of an aerosol either nasally or using delivery articles of the type set forth in U.S. Pat. No. 4,922,901 to Brooks et al., the disclosure of which is incorporated herein in its entirety); topically (e.g., in lotion form); or transdermally (e.g., using a transdermal patch, using technology that is commercially available from Novartis and Alza Corporation). Although it is possible to administer the compounds in the form of a bulk active chemical, it is preferred to present each compound in the form of a pharmaceutical composition or formulation for efficient and effective administration.

The compounds can be incorporated into drug delivery devices such as nanoparticles, microparticles, microcapsules, and the like. Representative microparticles/nanoparticles include those prepared with cyclodextrins, such as pegylated cyclodextrins, liposomes, including small unilamellar vesicles, and liposomes of a size designed to lodge in capillary beds around growing tumors. Suitable drug delivery devices are described, for example, in Heidel J D, et al., Administration in non-human primates of escalating intravenous doses of targeted nanoparticles containing ribonucleotide reductase subunit M2 siRNA, Proc Natl Acad Sci USA. 2007 Apr. 3; 104(14):5715-21; Wongmekiat et al., Preparation of drug nanoparticles by co-grinding with cyclodextrin: formation mechanism and factors affecting nanoparticle formation, Chem Pharm Bull (Tokyo). 2007 March; 55(3):359-63; Bartlett and Davis, Physicochemical and biological characterization of targeted, nucleic acid-containing nanoparticles, Bioconjug Chem. 2007 March-April; 18(2): 456-68; Villalonga et al., Amperometric biosensor for xanthine with supramolecular architecture, Chem. Commun. (Camb). 2007 Mar. 7; (9):942-4; Defaye et al., Pharmaceutical use of cyclodextrines: perspectives for drug targeting and control of membrane interactions, Ann Pharm Fr. 2007 January; 65(1):33-49; Wang et al., Synthesis of Oligo(ethylenediamino)-beta-Cyclodextrin Modified Gold Nanoparticle as a DNA Concentrator; Mol Pharm. 2007 March-April; 4(2): 189-98; Xia et al., Controlled synthesis of Y-junction polyaniline nanorods and nanotubes using in situ self-assembly of magnetic nanoparticles, J Nanosci Nanotechnol., 2006 December; 6(12):3950-4; and Nijhuis et al., Room-temperature single-electron tunneling in dendrimer-stabilized gold nanoparticles anchored at a molecular printboard, Small. 2006 December; 2(12):1422-6.

Exemplary methods for administering such compounds will be apparent to the skilled artisan. The usefulness of these formulations may depend on the particular composition used and the particular subject receiving the treatment. These formulations may contain a liquid carrier that may be oily, aqueous, emulsified or contain certain solvents suitable to the mode of administration.

The compositions can be administered intermittently or at a gradual, continuous, constant or controlled rate to a warm-blooded animal (e.g., a mammal such as a mouse, rat, cat, rabbit, dog, pig, cow, or monkey), but advantageously are administered to a human being. In addition, the time of day and the number of times per day that the pharmaceutical formulation is administered can vary.

Preferably, the compositions are administered such that active ingredients interact with regions where cancer cells are located. The compounds described herein are very potent at treating these cancers.

In certain circumstances, the compounds described herein can be employed as part of a pharmaceutical composition with other compounds intended to prevent or treat a particular cancer, i.e., combination therapy. In addition to effective amounts of the compounds described herein, the pharmaceutical compositions can also include various other components as additives or adjuncts.

Combination Therapy

The combination therapy may be administered as (a) a single pharmaceutical composition which comprises a noscapine/folic acid conjugate as described herein, at least one additional pharmaceutical agent described herein, and a pharmaceutically acceptable excipient, diluent, or carrier; or (b) two separate pharmaceutical compositions comprising (i) a first composition comprising a noscapine/folic acid conjugate as described herein and a pharmaceutically acceptable excipient, diluent, or carrier, and (ii) a second composition comprising at least one additional pharmaceutical agent described herein and a pharmaceutically acceptable excipient, diluent, or carrier. The pharmaceutical compositions can be administered simultaneously or sequentially and in any order.

In use in treating or preventing cancer, the conjugates described herein can be administered together with at least one other chemotherapeutic agent as part of a unitary pharmaceutical composition. Alternatively, the conjugates can be administered apart from the other anticancer chemotherapeutic agent. In this embodiment, the conjugates and the at least one other anticancer chemotherapeutic agent are administered substantially simultaneously, i.e. the compounds are administered at the same time or one after the other, so long as the compounds reach therapeutic levels for a period of time in the blood.

Combination therapy involves administering a noscapine/folic acid conjugate, as described herein, or a pharmaceutically acceptable salt or prodrug of a compound described herein, in combination with at least one anti-cancer chemotherapeutic agent, ideally one which functions by a different mechanism (i.e., VEGF inhibitors, alkylating agents, and the like).

Examples of known anticancer agents which can be used for combination therapy include, but are not limited to alkylating agents, such as busulfan, cis-platin, mitomycin C, and carboplatin; antimitotic agents, such as colchicine, vinblastine, paclitaxel, and docetaxel; topo I inhibitors, such as camptothecin and topotecan; topo II inhibitors, such as doxorubicin and etoposide; RNA/DNA antimetabolites, such as 5-azacytidine, 5-fluorouracil and methotrexate; DNA antimetabolites, such as 5-fluoro-2'-deoxy-uridine, ara-C, hydroxyurea and thioguanine; and antibodies, such as Herceptin® and Rituxan®. Other known anti-cancer agents, which can be used for combination therapy, include arsenic trioxide, gamcitabine, melphalan, chlorambucil, cyclophosamide, ifosfamide, vincristine, mitoguazone, epirubicin, aclarubicin, bleomycin, mitoxantrone, elliptinium, fludarabine, octreotide, retinoic acid, tamoxifen and alanosine. Other classes of anti-cancer compounds that can be used in combination with the conjugates are described below.

The conjugates can be combined with alpha-1-adrenoceptor antagonists, such as doxazosin, terazosin, and tamsulosin, which can inhibit the growth of prostate cancer cell via induction of apoptosis (Kyprianou, N., et al., Cancer Res 60:4550 4555, (2000)).

Sigma-2 receptors are expressed in high densities in a variety of tumor cell types (Vilner, B. J., et al., Cancer Res. 55: 408 413 (1995)) and sigma-2 receptor agonists, such as CB-64D, CB-184 and haloperidol, activate a novel apoptotic pathway and potentiate antineoplastic drugs in breast tumor cell lines. (Kyprianou, N., et al., Cancer Res. 62:313 322 (2002)). Accordingly, the conjugates can be combined with at least one known sigma-2 receptor agonists, or a pharmaceutically acceptable salt of said agent.

The conjugates can be combined with lovastatin, a HMG-CoA reductase inhibitor, and butyrate, an inducer of apoptosis in the Lewis lung carcinoma model in mice, can potentiate antitumor effects (Giermasz, A., et al., Int. J. Cancer 97:746 750 (2002)). Examples of known HMG-CoA reductase inhibitors, which can be used for combination therapy include, but are not limited to, lovastatin, simvastatin, pravastatin, fluvastatin, atorvastatin and cerivastatin, and pharmaceutically acceptable salts thereof.

Certain HIV protease inhibitors, such as indinavir or saquinavir, have potent anti-angiogenic activities and promote regression of Kaposi sarcoma (Sgadari, C., et al., Nat. Med. 8:225 232 (2002)). Accordingly (in addition to forming conjugates of these compounds), the conjugates can be combined with HIV protease inhibitors, or a pharmaceutically acceptable salt of said agent. Representative HIV protease inhibitors include, but are not limited to, amprenavir, abacavir, CGP-73547, CGP-61755, DMP-450, indinavir, nelfinavir, tipranavir, ritonavir, saquinavir, ABT-378, AG 1776, and BMS-232,632.

Synthetic retinoids, such as fenretinide (N-(4-hydroxyphenyl)retinamide, 4HPR), can have good activity in combination with other chemotherapeutic agents, such as cisplatin, etoposide or paclitaxel in small-cell lung cancer cell lines (Kalemkerian, G. P., et al., Cancer Chemother. Pharmacol. 43:145 150 (1999)). 4HPR also was reported to have good activity in combination with gamma-radiation on bladder cancer cell lines (Zou, C., et al., Int. J. Oncol. 13:1037 1041 (1998)). Representative retinoids and synthetic retinoids include, but are not limited to, bexarotene, tretinoin, 13-cis-retinoic acid, 9-cis-retinoic acid, α-difluoromethylornithine, ILX23-7553, fenretinide, and N-4-carboxyphenyl retinamide.

Proteasome inhibitors, such as lactacystin, exert anti-tumor activity in vivo and in tumor cells in vitro, including those resistant to conventional chemotherapeutic agents. By inhibiting NF-kappaB transcriptional activity, proteasome inhibitors may also prevent angiogenesis and metastasis in vivo and further increase the sensitivity of cancer cells to apoptosis (Almond, J. B., et al., Leukemia 16:433 443 (2002)). Representative proteasome inhibitors include, but are not limited to, lactacystin, MG-132, and PS-341.

Tyrosine kinase inhibitors, such as STI571 (Imatinib mesilate, Gleevec®), have potent synergetic effects in combination with other anti-leukemic agents, such as etoposide (Liu, W. M., et al. Br. J. Cancer 86:1472 1478 (2002)). Representative tyrosine kinase inhibitors include, but are not limited to, Gleevec®, ZD1839 (Iressa®), SH268, genistein, CEP2563, SU6668, SU11248, and EMD121974.

Prenyl-protein transferase inhibitors, such as farnesyl protein transferase inhibitor R115777, possess antitumor activity against human breast cancer (Kelland, L. R., et. al., Clin. Cancer Res. 7:3544 3550 (2001)). Synergy of the protein farnesyltransferase inhibitor SCH66336 and cisplatin in human cancer cell lines also has been reported (Adjei, A. A., et al., Clin. Cancer. Res. 7:1438 1445 (2001)). Prenyl-protein transferase inhibitors, including farnesyl protein transferase inhibitor, inhibitors of geranylgeranyl-protein transferase type I (GGPTase-I) and geranylgeranyl-protein transferase type-II, or a pharmaceutically acceptable salt of said agent, can be used in combination with the conjugates described herein. Examples of known prenylprotein transferase inhibitors include, but are not limited to, R115777, SCH66336, L-778,123, BAL9611 and TAN-1813.

Cyclin-dependent kinase (CDK) inhibitors, such as flavopiridol, have potent, often synergetic, effects in combination with other anticancer agents, such as CPT-11, a DNA topoisomerase I inhibitor in human colon cancer cells (Motwani, M., et al., Clin. Cancer Res. 7:4209 4219, (2001)). Representative cyclin-dependent kinase inhibitors include, but are not limited to, flavopiridol, UCN-01, roscovitine and olomoucine.

Certain COX-2 inhibitors are known to block angiogenesis, suppress solid tumor metastases, and slow the growth of implanted gastrointestinal cancer cells (Blanke, C. D., Oncology (Hunting) 16(No. 4 Suppl. 3):17 21 (2002)). Representative COX-2 inhibitors include, but are not limited to, celecoxib, valecoxib, and rofecoxib.

Any of the above-mentioned compounds can be used in combination therapy with the conjugates. Additionally, many of these compounds can be converted to conjugates by reaction of ketone, aldehyde, hydroxyl, thiol, and/or amine functional groups on the compounds using the chemistry described herein. The conjugates of these compounds are within the scope of this invention.

Further, the conjugates can be targeted to a tumor site by conjugation with therapeutically useful antibodies, such as Herceptin® or Rituxan®, growth factors, such as DGF, NGF; cytokines, such as IL-2, IL-4, or any molecule that binds to the cell surface. The antibodies and other molecules will deliver a compound described herein to its targets and make it an effective anticancer agent. The bioconjugates can also enhance the anticancer effect of therapeutically useful antibodies, such as Herceptin® or Rituxan®.

The compounds can also be used in conjunction with surgical tumor removal, by administering the compounds before and/or after surgery, and in conjunction with radiation therapy, by administering the compounds before, during, and/or after radiation therapy.

The appropriate dose of the compound is that amount effective to prevent occurrence of the symptoms of the disorder or to treat some symptoms of the disorder from which the patient suffers. By "effective amount", "therapeutic amount" or "effective dose" is meant that amount sufficient to elicit the desired pharmacological or therapeutic effects, thus resulting in effective prevention or treatment of the disorder.

When treating cancers, an effective amount of the conugates described herein is an amount sufficient to suppress the growth of the tumor(s), and, ideally, is a sufficient amount to shrink the tumor, and, more ideally, to destroy the tumor. Cancer can be prevented, either initially, or from re-occurring, by administering the compounds described herein in a prophylactic manner. Preferably, the effective amount is sufficient to obtain the desired result, but insufficient to cause appreciable side effects.

The effective dose can vary, depending upon factors such as the condition of the patient, the severity of the cancer, and the manner in which the pharmaceutical composition is administered. The effective dose of compounds will of course differ from patient to patient, but in general includes amounts starting where desired therapeutic effects occur but below the amount where significant side effects are observed.

The compounds, when employed in effective amounts in accordance with the method described herein, are selective to certain cancer cells, but do not significantly affect normal cells.

For human patients, the effective dose of typical compounds generally requires administering the compound in an amount of at least about 1, often at least about 10, and frequently at least about 25 μg/24 hr/patient. The effective dose generally does not exceed about 500, often does not exceed about 400, and frequently does not exceed about 300 μg/24 hr/patient. In addition, administration of the effective dose is such that the concentration of the compound within the plasma of the patient normally does not exceed 500 ng/mL and frequently does not exceed 100 ng/mL.

III. Methods of Treatment

The compounds described herein, and pharmaceutical compositions including the compounds, can be used to treat various cancers, particularly metastatic cancers, and tumors overexpres sing folic acid receptors. Examples of such tumors include ovarian, breast, cervical, a highly metastatic prostate PC3 and glioma cancer cells (U87), all of which show high levels of FR-α receptor.

Representative malignant tumors include malignant endothelial tumors such as melanoma. Additional cancers that can be treated include, but not limited to human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, and heavy chain disease, and malignant forms of these cancers.

In one embodiment, the cancer is melanoma, rectal carcinoma, colon carcinoma, breast carcinoma, ovarian carcinoma, small cell lung carcinoma, colon carcinoma, chronic lymphocytic carcinoma, hairy cell leukemia, esophogeal carcinoma, prostate carcinoma, breast cancer, myeloma, or lymphoma.

In some embodiments, the patient already has cancer and is undergoing treatment for the cancer, and may or may not have tumor metastasis (i.e., secondary cancer).

The conjugates can also be used to treat other types of disorders, such as those cellular disorders known to be treated by folic acid and/or noscapine. The term "cellular disorders" is intended to encompass neoplasms and other hyperplastic conditions, whether benign or malignant, which are amendable to treatment using folic acid analogs as well as conditions such as rheumatoid arthritis which is amendable to treatment using folic acid analogs. Such cellular disorders include but are not limited to: uterine choriocarcinoma, chorioma, chorioadenoma destruens, hydatidiform mole, acute and subacute leukemias, leukemic menigitis, lymphosarcoma, mycosis fungoides, lung cancers particularly squamous and small cell types, osteogenic sarcoma, certain tumors of the head, neck and pelvis, severe disabling psoriasis and rheumatoid arthritis.

IV. Diagnostic Methods

In some embodiments, the noscapine/folic acid analogs are labeled with a suitable label such that they can be used in diagnostic methods to identify the presence of cancer, for example, metasticized cells distant from the original tumor site.

One example illustrating how folic acid can be radiolabeled is shown in Bettio et al. ("Synthesis and preclinical evaluation of a folic acid derivative labeled with $^{18}$F for PET imaging of folate receptor-positive tumors," Journal of nuclear medicine, 2006, vol. 47, no7, pp. 1153-1160)). Bettio prepared radiolabeled folic acid analogs, and used them in imaging studies to identify tumors. The identity of tumors was confirmed by measuring radiolabel concentration adjacent to, or inside the tumor cells, resulting from the binding of the conjugates to the tumor cells.

Bettio regioselectively linked folic acid through its α- and γ-carboxyl groups to 4-fluorobenzylamine (FBA), and the α- and γ-FBA-folate regioisomers effectively bound folate receptor-positive cells. The $^{18}$F-labeled α/γ-FBA-folate counterpart was examined for in vivo tumor targeting efficiency in nude mice bearing folate receptor-positive tumor cells.

The $^{18}$F-α/γ-FBA-folate was prepared in a 4-step reaction sequence starting from folic acid. The relative binding affinities of the α- and γ-FBA-folates to the folate receptor with respect to parent folic acid were determined in cultured KB-31 cells (nasopharyngeal epidermal carcinoma cell line) overexpressing the folate receptor using $^3$H-folic acid.

Bettio analyzed tumor accumulation of the $^{18}$F-labeled α/γ-FBA-folate and $^{18}$F-FDG in vivo by high-resolution PET. Biodistribution and PET studies were performed under baseline and blockage conditions. Results: The radiochemical yield of the coupling step ranged from 15% to 44%, and the maximum specific radioactivity was 24 GBq/μmol. The in vitro binding affinities of the α- and γ-isomers and folic acid were 71, 62, and 41 nmol/L, respectively. PET revealed heterogeneous uptake of the radioligand, with the highest activity concentrations found in the tumor rim. In contrast, $^{18}$F-FDG uptake in a nude mouse bearing KB-31 folate receptor-positive tumors was negligible. Radioligand uptake in tumors at 125 min after injection amounted to 6.56% of the injected dose per gram of tissue (% ID/g) in control animals, whereas radioactivity accumulation in the tumors of folic acid-treated animals was significantly reduced by more than 80%- to 1.07% ID/g (P=0.001). Thus, $^{18}$F-labeled folic acid derivatives can be used as precursors for conjugating with the noscapine analogs, with the resulting conjugates used for PET imaging of folate receptor-positive tumors. The resulting conjugates can be used in an analogous fashion to the $^{18}$F radiolabeled folic acid.

These compounds can easily chelate $^{m99}$Tc in its folate moiety and thus can serve as non-invasive diagnostic/prognostic imaging tools for FR-alpha positive cancers.

Other radiolabeled folic acid analogs, which can be used to prepare radiolabeled conjugates with noscapine or noscapine analogs, are disclosed, for example, in U.S. Pat. No. 7,128,893.

The following examples are provided to illustrate the present invention, and should not be construed as limiting thereof. In the synthetic examples, all parts and percentages are by weight, unless otherwise noted. Reaction yields are reported in mole percentages.

Example 1

Anti-Tumor Activity of Noscapine

Assembly of microtubules (MTs), a ubiquitous cellular polymer, made up largely of a dimer subunit of α- and β-tubulins, is highly dynamic throughout the life of a eukaryotic cell. MTs are essential for many cellular processes such as the establishment of polarity, directed cell migration, growth, and intracellular transport of various macromolecules/vesicles and organelles including chromosomes during cell division.

In a MT population at a steady state, many individual microtubules are in a growing phase while others are in a shortening phase. This is achieved because of the inherent stochastic transitions between the two phases of polymerization and depolymerization of individual MTs, which is interrupted occasionally by a pause state when neither growth nor shortening is detected (Gould and Borisy, 1977; Mitchison and Kirschner, 1984a, 1984b; Cassimeris et al., 1987; Kirschner and Mitchison, 1986, Derry et al., 1995; Dhamodharan et al., 1995; Panda et al., 1996; Joshi, 1998; Jordan and Wilson, 1999).

When cells make the decision to enter the cell division cycle, they duplicate their DNA content as well as the centrosome, which serves as a center of nucleation for MT assembly (Brinkley et al., 1985; Oakley et al., 1990; Sterns and Kirschner, 1990; Joshi et al., 1992) Like DNA, centrosomes duplicate once during the S-phase to prepare for subsequent mitosis. During this phase, the dynamics of MTs increases up to ten-fold, which is required to rapidly form a functional bipolar mitotic spindle. This bipolar array must then align each of the duplicated chromatid pairs at the center of the mitotic spindle before separation to opposite poles of the spindle in anaphase.

Unattached chromosomes or damaged spindles inhibit the onset of anaphase, cytokinesis, and subsequent DNA replication of the next cell cycle via arrays of signal transduction pathways, collectively called the cell cycle checkpoints (Chen et al., 1996; Lanni and Jacks, 1998). Together, these checkpoints ensure the accurate transmission of each chromatid to daughter cells.

Normal, healthy cells are able to detect errors such as damage to the MT-spindle, DNA, or misregulation of growth signals, and in response arrest cell cycle at various stages until the damage/error is fixed. Only then do cells resume the precisely orchestrated sequence of cell cycle events. Thus, the checkpoint mechanisms save cells from catastrophic biochemical stress caused by excessive polyploidy, aneuploidy, or aploidy leading to the initiation of fatal cascades that culminate in programmed cell death (apoptosis).

Chemical-genetic approaches have not only elucidated the molecular mechanisms of cell cycle regulation, but have provided life saving tools for the clinical management of patients suffering from otherwise lethal diseases of the cell cycle, the most important class being cancer. Among the chemotherapeutic targets for various types of cancers, all the crucial events of the cell cycle have been exploited (e.g. DNA replication, signal transduction, damage to DNA, and most recently damage to MTs by causing their depolymerization or overpolymerization and bundling). These approaches work primarily because they induce apoptosis in rapidly dividing cancer cells but also kill normal cells, causing toxicities to leukocytes (hence leukocytopenia and immunosuppression), epithelia of digestive system (hence diarrhea and nausea), hair follicles (hence alopecia), among others. They have to be infused intravenously over long periods of time in biologically-incompatible solvents, causing hypersensitive reactions in some cases. In addition, in non-mitotic cells such as neurons with their long axons, these agents interrupt the axonal transport process, which is vital for the maintenance of their structural integrity and function, causing neuropathies particularly in the peripheral extremities (Rowinsky et al., 1997; Wang et al., 2000).

In contrast, noscapine is a tubulin-binding, non-toxic, blood-barrier-crossing, anti-cancer agent (Ye et al., 1998; Joshi and Zhou, 2000). Noscapine is a plant-derived alkaloid with a long-history of human use as an anti-cough agent. Noscapine is non-toxic even in large experimental doses (1-2 gm a day), and is orally available (its plasma concentration peaks at 2.5 to 3 hours after oral ingestion, and is non-detectable after 5.5 hours in plasma) (Dahlstrom et al., 1982; Karlsson et al., 1990).

Current anti-MT drugs either completely eliminate MTs (e.g., colchicines, MTC, podophyllotoxin), or depolymerize MTs but form aberrant paracrystals of tubulin (e.g., vinca family), or overpolymerize cellular microtubules (e.g., taxane family). These agents arrest dividing cells in pro-metaphase.

Figure 1A:
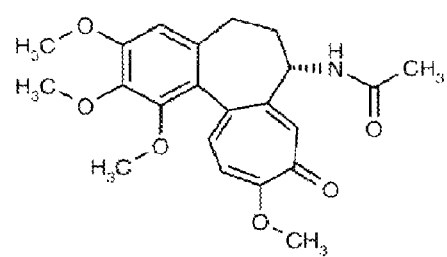
FIG. 1A shows the chemical structures of colchicine, MTC, podophyllotoxin, and noscapine.
Figure 1A:
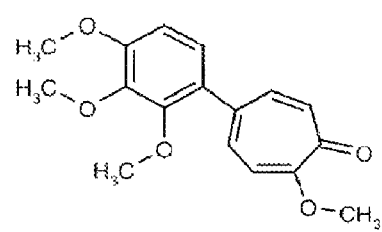
Figure 1A:
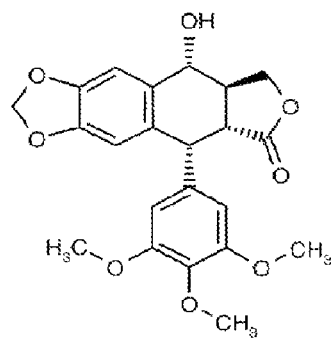
Figure 1A:
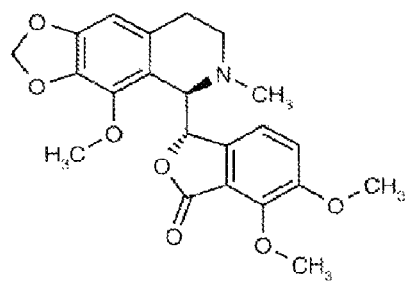

Initial studies focused on the chemical structures of simple agents that are known to depolymerize MTs (i.e., the colchicines, MTC, podophyllotoxin-family), which cannot be used clinically for cancer treatment because of their extreme toxicity. The goal was to identify a chemical variant of this family of compounds that did not cause complete MT depolymerization, thus maintaining total polymer mass of MTs, but altered MT dynamics just enough to activate the mitotic checkpoint to cause mitotic arrest (Ye et al., 1998). Thus by examining the structures of colchicine, podophyllotoxin, MTC [2-methoxy-5-(2,3,4-trimethoxyphenyl)-2,4,6-cycloheptatrien-1-one], and other members of this class, the present inventor noticed that many of these compounds contain a hydrophobic trimethoxyphenyl group, a variety of other hydrophobic domains such as lactone, tropolone, or other aromatic rings, and small hydrophilic group/s such as hydroxyl and amino groups. Structurally similar agents that can engage mitotic checkpoints without causing gross deformations of cellular microtubules even at high concentrations were screened, examples of which are shown in FIG. 1A, one of which is noscapine.

Figure 1B:
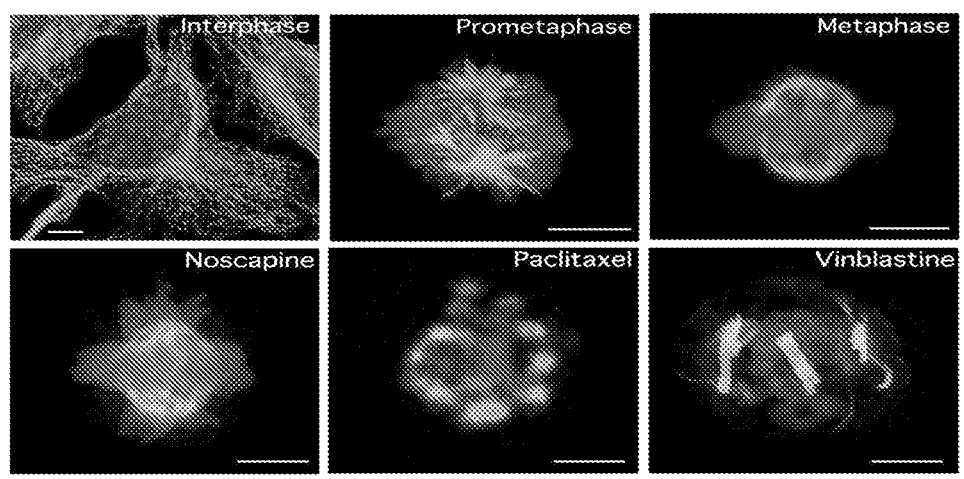
FIG. 1B shows immunofluorescence micrographs of microtubule arrays (green) and DNA (red) in control interphase, prometaphase, and metaphase cells and in cells arrested by anti-microtubule drugs. Noscapine-arrested cells have nearly normal bipolar spindles (with chromosomes in red are lagging and have failed to arrive at the mid-plate) whereas in paclitaxel-arrested cells, microtubules form dense asters tethered with chromosomes. In vinblastine-arrested cells, the tubulin subunits resulting from spindle depolymerization form large paracrystalline structures. Bar, 10 μm. This phenomenon was observed in all mammalian cells including gliomas, ovarian, breast, melanoma and cervical cancer types that also arrest briefly in this stage before slipping through the arrest abortively into the next cell cycle (Zhou et al., 2005; Landen et al., 2002, 2004; Aneja et al 2006a, 2006b, 2006c).

Noscapine arrests mitosis without microtubule depolymerization. FIG. 1B shows immunofluorescence micrographs of microtubule arrays (green) and DNA (red) in control interphase, prometaphase, and metaphase cells and in cells arrested by anti-microtubule drugs. Noscapine-arrested cells have nearly normal bipolar spindles (with chromosomes in red are lagging and have failed to arrive at the mid-plate) whereas in paclitaxel-arrested cells, microtubules form dense asters tethered with chromosomes. In vinblastine-arrested cells, the tubulin subunits resulting from spindle depolymerization form large paracrystalline structures. Bar, 10 µm. This phenomenon was observed in all mammalian cells including gliomas, ovarian, breast, melanoma and cervical cancer types that also arrest briefly in this stage before slipping through the arrest abortively into the next cell cycle (Zhou et al., 2005; Landen et al., 2002, 2004; Aneja et al 2006a, 2006b, 2006c).

The next issue to address was whether noscapine shared the properties of other trimethoxyphenyl group compounds. The questions were whether noscapine binds tubulin, whether it changes the total polymer mass, whether it alters the MT dynamics of in vitro assembled MTs from purified tubulin, and whether it does so in vivo in the intracellular milieu. The answer to all the questions was favorable (Ye et al., 1998; Zhou et al., 2002; Landen et al., 2002). Noscapine bound avidly to tubulin with an apparent stoichiometry of 0.95±0.02 noscapine molecule per tubulin dimer subunit, although the possibility of two equal affinity binding sites on tubulin could not be excluded (Ye et al., 1998). Noscapine does not alter the total polymer/subunit ratio of tubulin in cells when measured biochemically (Zhou et al. 2002).

Figure 2:
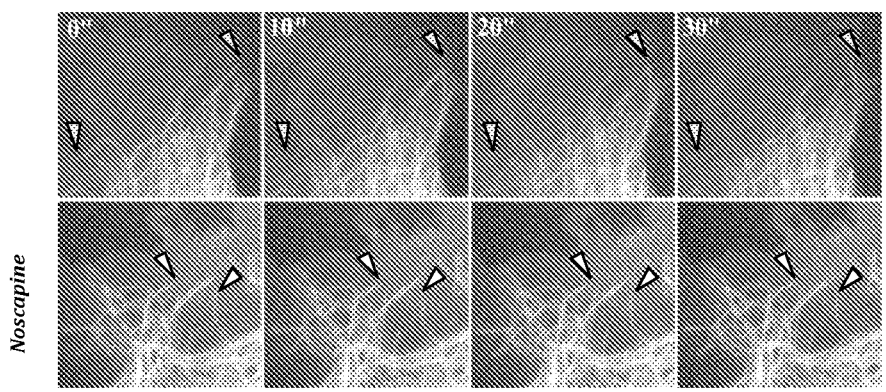
FIG. 2 is a series of video frames, taken 10 seconds apart, of the plus ends of several microtubules (MTs) in control and noscapine-treated cells. The video frames show that noscapine increases the average time cellular MTs remain inactive (pause duration). As expected in control cells, MTs alternated between phases of growth and shortening. Thus, the position of their plus ends changed significantly over 30 seconds (fixed pixel locations marked with arrowheads). In contrast, noscapine-treated cells markedly suppressed MT dynamics as indicated by the unaltered positions of their plus ends.

The effect of noscapine on MT dynamics at steady state in vitro from purified tubulin was evaluated. The results showed that MTs spend longer periods of time in "pause" or attenuated state when treated with noscapine as compared to the untreated samples. The details of these studies are published (Zhou et al., 2002). To determine if noscapine also affects MT dynamics in living cells, the life history of the plus ends of cellular MTs, resolvable individually at the cell periphery of cells expressing green fluorescent protein (GFP)-tagged α-tubulin, was followed (Landen et al., 2002). These cells were treated either with noscapine in DMSO or DMSO alone. FIG. 2 shows an example of a gallery of video frames, 10 seconds apart, of the plus ends of several MTs in control and noscapine treated cells. As expected in control cells, MTs alternated between phases of growth and shortening interrupted occasionally by a state of attenuated dynamic activity (pause), determined by noting the position of the plus ends over time. FIG. 2 shows different positions of MT plus ends in a 30 second time period (arrows represent fixed pixel position for reference). In contrast, noscapine-treated cells showed suppressed MT dynamics as indicated by unaltered location of their plus ends over the 30 second time period. These data suggest that noscapine prevents the number of dynamic events in the life history of a MT without affecting its long-term existence. Detailed results were published (Landen et al., 2002; Zhou et al, 2002).

Detailed studies of the cell cycle progression of various cancer cells were conducted in the presence or absence of noscapine. Noscapine induced a brief mitotic pause followed by extensive apoptosis of many cancer cell types including melanoma, glioblastoma, ovarian, breast carcinoma, and prostate cancer cells. Detailed in vitro experiments revealed that the apoptosis was preceded by abnormal mitoses, often multi-polar, extensive polyploidy (up to 16N DNA), increased JNK, reduced AKT signaling, an increase in the ratio of pro-apoptotic/anti-apoptotic proteins, a drop in mitochondrial transmembrane potential, cytochrome-C release, abnormal externalization of phosphatidyl-serine from the inner to the outer leaflet of the plasma membrane, activation of the executionery caspases (caspase-7 and caspase-3), the cleavage of their substrates, DNA hypercondensation, and internucleosomal fragmentation of DNA (Ye et al., 1998; Ke et al., 2000; Ye et al., 2001; Zhou et al., 2002a, b; Landen et al., 2002; Zhou et al., 2003; Joshi and Zhou, 2000; Landen et al., 2004; Zhou et al., 2005; Aneja et al., 2006a, 2006b, 2006c, 2006d, 2006e, 2006f, 2007a).

The next step was to investigate whether noscapinoids (i.e., noscapine and the noscapine analogs described herein) caused apoptosis of in vivo xenografts of human tumors in immuno-compromised nude mice. Although complete remission of tumors in these models was not achieved, a striking reduction in tumor mass and growth, particularly for ovarian, breast, prostate cancer, lymphoma, thymoma, and brain-glioblastomas, was observed (Ye et al., 1998; Zhou et al., 2002, 2005; Aneja et al., 2006a, 2006b, 2006c; Landen et al., 2004). Pharmacokinetic studies as well as the existing previous literature on this subject (because of its anti-cough activity) clearly showed a short systemic life of noscapine in animals (Aneja et al., 2007; Dahlstrom et al., 1982; Karlsson et al., 1990). Furthermore, the drug bioavailability did not increase even after doubling the oral dose of 300 mg/kg body weight to 600 mg/kg. There was however, no toxicity detected at the higher dose.

The present inventors sought a novel, targeted approach aimed at preventing and treating recurrence of aggressive tumors, for example, ovary, breast, prostate, and brain tumors. While not wishing to be bound to a particular theory, it is believed that by using the naturally overexpressed folate receptor-α (FR-α) in many ovarian-, breast-, prostate-, and brain-cancers (mostly gliomas and pituitary adenomas), we can target noscapine in high concentrations to the tumor cells without reducing its anti-cancer activity, and hence prevent, treat and achieve prolonged disease-free survival in preclinical models. This mechanism is supported by the data presented in the following examples.

Example 2

Expression of Folate Receptor-α (FR-α) in Cancer Cells

Many aggressive tumors overexpress FR-α. The rationale behind this example was to identify tumors which overexpress FR-α, and which would then be a target for noscapine, in order to compare the anti-tumor properties of noscapine and a folate conjugate of noscapine against such tumors results.

Figure 3:
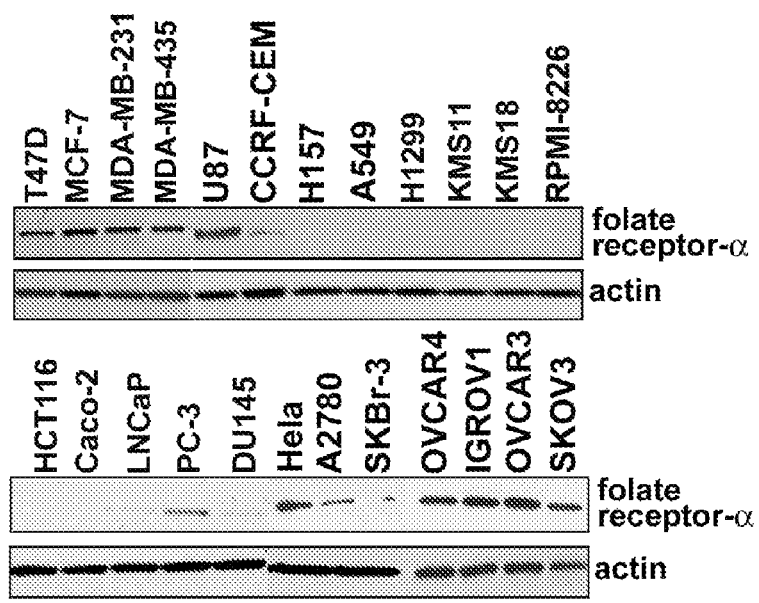
FIG. 3 is a representative western blot showing the expression of FR-α in a variety of cancer cell lines from different tissue origins. Actin was used as a loading control.

Thus, a panel of 24 cancer cell lines of different tissue origins such as breast (T47D, MCF-7, MDA-MB-231, MDA-MB-435, SKBr$_3$), lymphoma (CCRF-CEM, RPMI-8226), multiple myeloma (KMS11, KMS18), brain glioma (U87), colon (HCT116, Caco-2), lung (H157, H1299, A549), prostate (DU145, highly metastatic PC-3, LNCaP), cervical (Hela), and ovarian (OVCAR3, OVCAR4, IGROV1, SK-OV3, A2780) was screened for their expression of FR-α using a specific antibody against FR-α (LK-26) by immunoblotting techniques (FIG. 3). It was found that all ovarian, breast, cervical, a highly metastatic prostate PC3 and glioma cancer cells (U87) showed high levels of FR-α receptor. These results provided strong impetus to pursue the rational synthesis of a folate conjugate of noscapine (described herein as "Targetin").

Example 3

Rational Basis of Synthesis, Purification, and Validation of Noscapine-Folate Conjugates Having identified cell lines with which to compare noscapine with noscapine-folate conjugates, the next goal was to identify a site on the noscapine molecule where a folic acid group can be conjugated without losing the biological activity of noscapine.

Example 3

Figure 4:
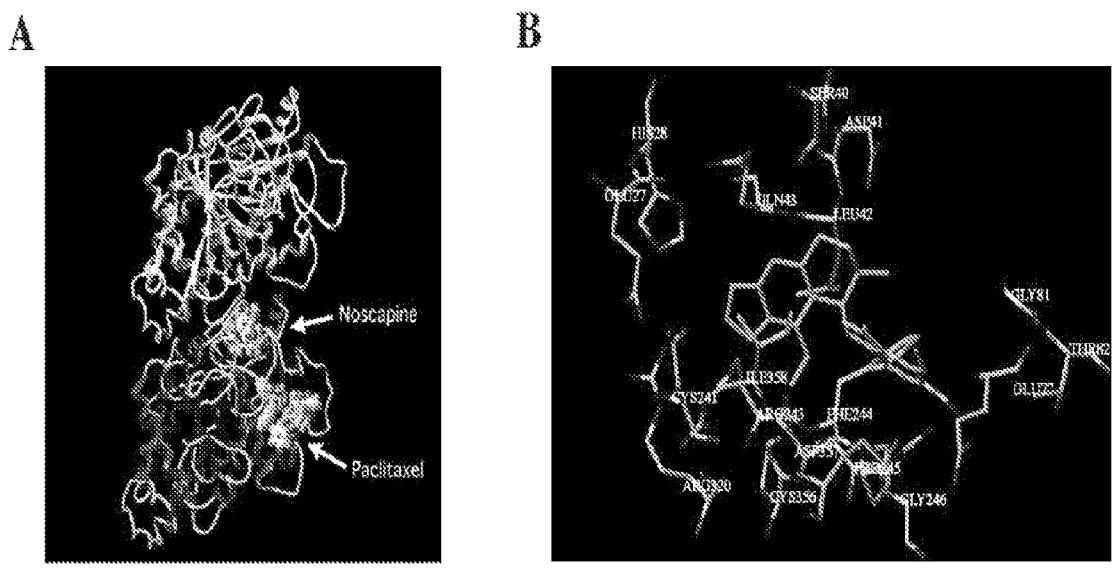
FIGS. 4A and 4B are space-filling models showing the structural interaction of noscapine with β-tubulin. In (4A), noscapine was docked into a pocket of β-tubulin beneath the interaction surface of β-tubulin and α-tubulin in the tubulin heterodimer. This pocket is different from that for paclitaxel. (4B) Details of important binding of noscapine (yellow scheme) with the side chains of β-tubulin.

Rational Basis of Synthesis, Purification, and Validation of Noscapine-Folate Conjugates Having identified cell lines that overexpress FR-α, we wished to take advantage of this property of cancer cells to design a folate-noscapine conjugate drug (Targetin) that retains the anti-cancer activity of noscapine. Two lines of experiments, structure-activity analysis and in silico modeling analysis, pointed to an acidic proton at the C-9 position of noscapine as a representative location on the noscapine molecule that can be derivatized with a folate group. The 9-position is well placed to accommodate large groups, because a large flexible tubulin loop loomed around this position to the outer lateral side of the interface between α- and β-tubulin subunits (FIG. 4). Prior efforts by the present inventors have included the preparation and characterization of other noscapine analogues substituted at the 9-position, for example, with halogens. The present efforts involve the preparation of amino-, nitro-, azido- and folate groups. Based on our predictions based on the in silico efforts, in many cases, the derivatives not only remained active, but also became more potent against cancer cells without being toxic (Aneja et al., 2006a, 2006d; Zhou et al., 2003; Checchi et al., 2003).

Synthesis of a Noscapine-Folate Conjugate:

Targetin was synthesized using a four-step synthetic scheme, as illustrated below. Noscapine (1) was brominated by adding 48% hydrobromic acid and freshly prepared bromine water. The reaction mixture was stirred for 1 hr at 25° C., and basified to pH 10 to yield 9-bromonoscapine (2) in ~82% yield. Refluxing compound 2 in dimethyl formamide with sodium azide and sodium iodide for 15 hrs gave the corresponding azido derivative (3), which when reduced with tin chloride in the presence of thiophenol and triethylamine in tetrahydrofuran for 2 hrs at 25° C. to provide 9-aminonoscapine (4) in ~83% yield.

Noscapine-folate (Targetin, 6) was synthesized by coupling folic acid activated ester, folate-NHS (5) to 9-aminonoscapine (4). The γ-carboxylic group of folic acid (7) was not reactive, and, hence, was activated using N-hydroxysuccinimide and dicyclohexylcarbodiimide as coupling reagents in DMSO to provide NHS-folate (5). Compound 5 was then reacted (in the dark) with 9-aminonoscapine (4) for 12 hrs in dimethyl sulfoxide to obtain Targetin (6) in ~72% yield.

All intermediates were well-characterized spectrally using $^1$H NMR (400 MHz, referenced with residual chloroform (7.27 ppm)) and $^{13}$C NMR (100 MHz, referenced with 77.27 ppm resonance of residual chloroform). Infrared spectra were recorded on sodium chloride discs on Mattson Genesis II FT-IR. High resolution mass spectra (HRMS) were collected on Thermo Finnigan LTQ-FT Hybrid mass spectrophotometer using 3-nitrobenzyl alcohol, in some cases with addition of LiI as a matrix. The spectral data are provided below, following the reaction scheme, Scheme 1. Targetin was then purified further by column chromatography to yield a >98% pure sample.

Scheme I - Synthesis of Targetin:

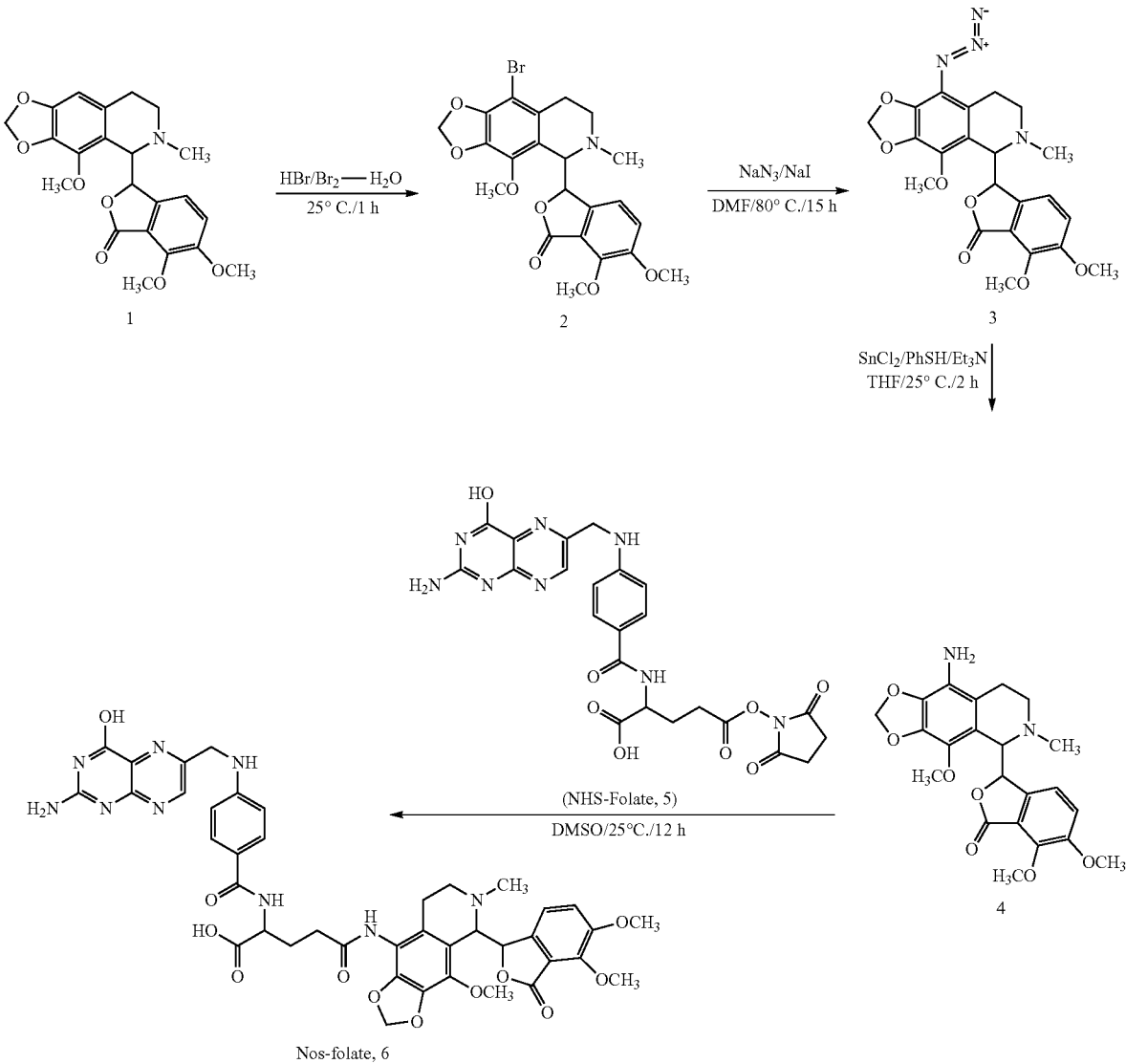

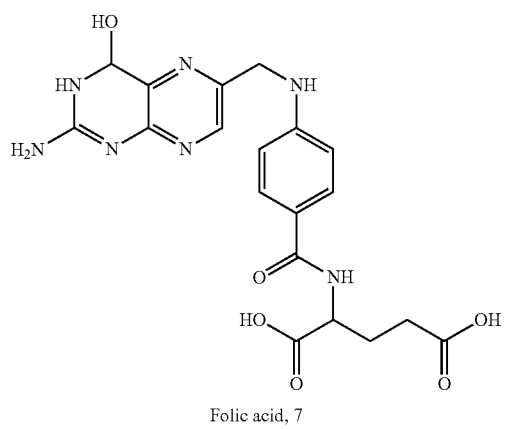

Folic acid, 7

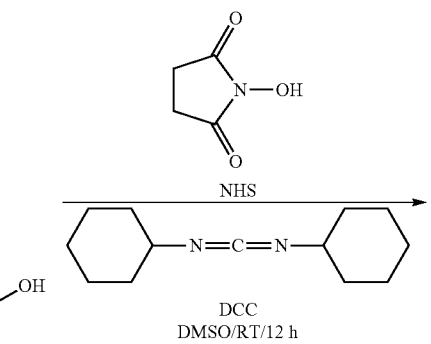

NHS

DCC
DMSO/RT/12 h

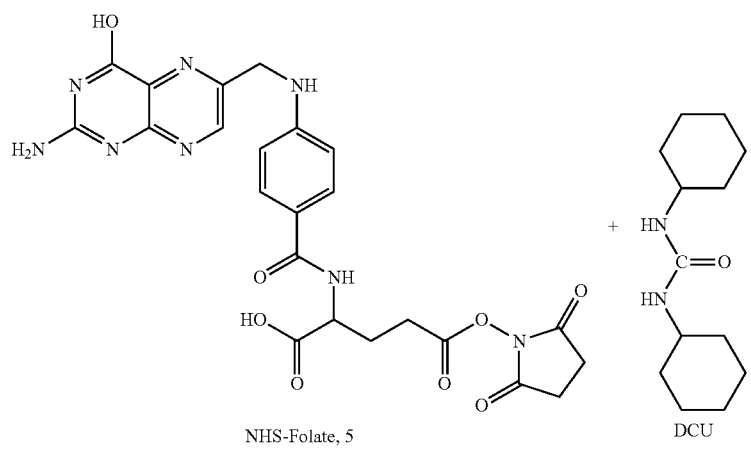

NHS-Folate, 5 + DCU

Spectral Details for Characterization of Targetin (6):

Yield: 72%; mp 123-124° C.; IR: 2945 (m), 2800 (m), 1759 (s), 1612 (m), 1500 (s), 1443 (s), 1263 (s), 1091 (s), 933 (w) cm$^{-1}$; $^1$H NMR (CDCl$_3$, 400 MHz), δ 11.44 (s, 1H), 8.64 (s, 1H), 8.14 (s, 1H), 8.11 (s, 1H), 7.66 (d, 1H, J=6.1 Hz), 7.63 (d, 1H, J=6.1 Hz), 7.27 (d, 1H, J=6.1 Hz), 7.25 (d, 1H, J=6.1 Hz), 6.95 (t, 1H, J=2.2 Hz), 6.65 (d, 1H, J=4 Hz), 5.99 (s, 4H), 5.53 (d, 2H, J=4 Hz), 4.49 (bs, 1H), 3.94 (s, 3H), 3.86 (s, 3H), 3.79 (s, 3H), 3.34 (s, 4H), 2.56-2.45 (m, 7H), 2.40-2.25 (m, 4H); $^{13}$C NMR (CDCl$_3$, 100 MHz), δ 175.2, 171.8, 168.1, 167.5, 163.4, 162.1, 152.8, 149.7, 145.8×3, 143.9, 141.0, 138.3, 134.0, 129.1×2, 127.2, 120.9×2, 119.9, 117.8, 115.9, 114.8, 113.4×2, 90.5, 83.5, 82.8, 70.6, 58.5, 57.0×2, 56.5×3, 52.0, 36.4, 28.2, 27.0, 22.1; HRMS (ESI): m/z Calculated for C$_{41}$H$_{43}$N$_9$O$_{12}$ (M+1), 853.8312; Experimentally determined, 854.7522 (M+1).

Example 4

Figure 5:
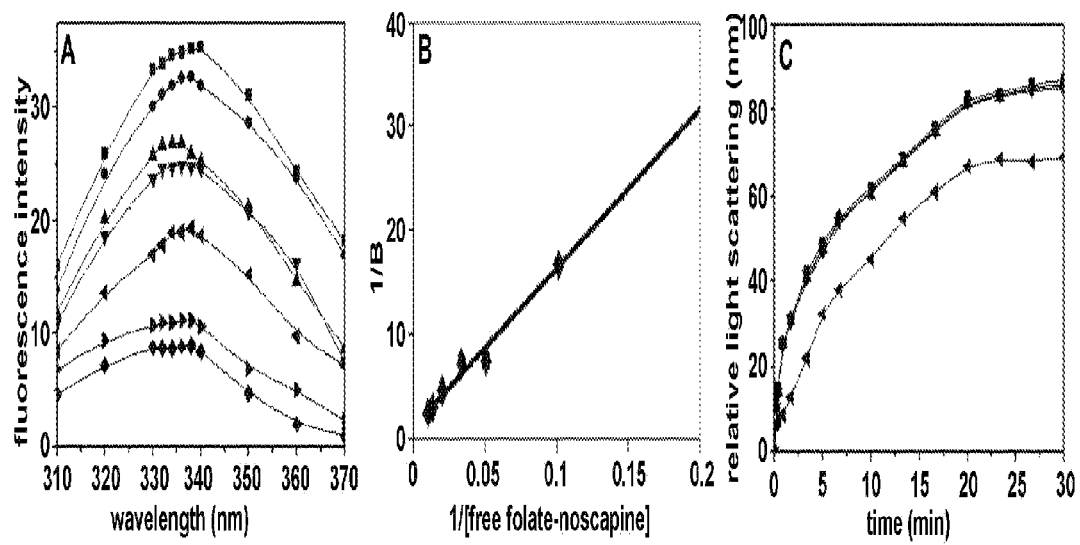
FIG. 5 is a picture showing the fluorescence quenching of tubulin by Targetin. Panel A, quenching of tubulin fluorescence emission by Targetin in a concentration-dependent manner (■) control, 10 μM (●), 20 μM (▲), 30 μM (▼), 50

Comparison of Tubulin Binding and Effect on Tubulin Polymerization of Targetin and Noscapine The next step was to determine whether Targetin retained the tubulin-binding property of the parent compound noscapine, without substantially altering tubulin polymerization. As shown below by the standard tubulin-fluorescence quenching titration, Targetin does retain the tubulin binding activity (FIGS. 5 A & B) of the parent compound noscapine (Ye et al., 1998). In addition, the effect of Targetin on the assembly of tubulin subunits into microtubules in vitro, measured by changes in light scattering upon tubulin polymerization, show that like noscapine, Targetin did not inhibit tubulin polymerization at 25 μM concentration. However, at a four-fold concentration of Targetin (100 μM), it inhibited the rate and extent of tubulin polymerization by ~17% (FIG. 5C).

Example 5

Effect of Targetin on Microtubule Dynamics In Vivo

To determine if Targetin affects MT dynamics in living cells, the life history of the plus ends of Targetin-treated cellular MTs was evaluated, resolvable individually at the cell periphery of porcine renal LLCPK-1 cells stably expressing green fluorescent protein (GFP)-tagged α-tubulin. These cells were treated either with Targetin in DMSO or DMSO alone. FIG. 6 shows a gallery of video frames, 6 seconds apart, of the plus ends of several MTs in control and Targetin treated cells. As expected in control cells, MTs alternated between phases of growth and shortening interrupted occasionally by a state of attenuated dynamic activity (pause), determined by noting the position of the plus ends over time. The control panels show different positions of MT plus ends in a 24 second time period (arrows represent fixed pixel position for reference). In contrast, Targetin-treated cells showed suppressed MT dynamics as indicated by unaltered location of their plus ends over the 24 second time period. The detailed data are presented in Table I. These data show that Targetin treatment prevents the number of dynamic events in the life history of a MT without affecting its long-term stability.

TABLE 1

Quantitative effect of Targetin on the dynamics of
individual microtubules in interphase cells

| | Targetin (μM) | | |
|---|---|---|---|
| Parameter | 0 | 5 | 10 |
| Rate (μm/min) | | | |
| Growing | 9.15 ± 2.72 | 8.72 ± 1.32 | 7.15 ± 0.56 |
| Shortening | 12.04 ± 2.81 | 11.78 ± 1.21 | 9.92 ± 1.25 |
| Percent of total time | | | |
| Growing | 41.8 | 35.2 | 24.3 |
| Shortening | 36.3 | 28.5 | 20.1 |
| Attenuation | 21.8 | 32.5 | 44.8 |
| Transition frequency (sec$^{-1}$) | | | |
| Catastrophe | 0.086 ± 0.02 | 0.079 ± 0.07 | 0.072 ± 0.05 |
| Rescue | 0.077 ± 0.01 | 0.07 ± 0.012 | 0.059 ± 0.019 |
| Dynamicity (μm/min) | 6.61 ± 2.36 | 4.52 ± 1.21 | 2.75 ± 1.05 |
| Average pause (sec) | 8.16 ± 2.42 | 10.25 ± 1.25 | 14.52 ± 2.36 |

Example 6

Comparison of the Sensitivity of
Folate-Overexpressing Cancer Cells to Targetin
Treatment vs. Noscapine Treatment, and
Demonstration that Free Folic Acid Competes with
Targetin Our next goal was to determine whether differences in folate receptor overexpression affected cytotoxicity in response to Targetin. To this end, the ability of Targetin to inhibit cellular proliferation of a variety of cancer cell types with varying degrees of folate receptor expression was evaluated using a sulforhodamine B assay to determine total protein content (FIG. 7). The data showed that Targetin was generally more potent (about 3 fold) than noscapine, irrespective of folate receptor status. FIG. 7 shows only a few cell lines as representative samples.

Next, an analysis of whether Targetin is more toxic to FR-α overexpressing cancer cells, and if the toxicity was FR-α mediated, was performed. Towards this end, a few lines overexpressing FR-α and those that express FR-α at a non-detectable level were selected. Two representative cell lines are shown below, though this experiment has been performed with four different cell types with consistent data (data not shown).

An equal number of two types of cells, (SK-OV3 human ovarian carcinoma cells and U87 glioblastoma cells) were plated in 15 tissue culture dishes. Plates were divided into five groups of triplicates. Group 1 received vehicle solution (DMSO), group 2 received 25 μM noscapine, group 3 received 10 μM Targetin, group 4 received 50 μM folic acid and group 5 received 50 μM folic acid+10 μM Targetin, each for 48 hours.

FIGS. 8A & B show phase images and quantification of cell viability using Trypan blue in SK-OV3 cells. FIGS. 8C & D show parallel data for human glioblastoma U87 cells. Data for two other FR-α cell lines are similar (not shown). Collectively, these data clearly show that Targetin treatment is significantly more effective than noscapine in all FR-α overexpressing cell lines that have been tested to date (four). Since free folic acid mitigates the Targetin toxicity to the FR-α overexpressing cancer cells, but not in cells that do not express FR-α at high levels, the observed augmented activity of Targetin was most likely to be folate-mediated.

Summary

The data are founded on our initial discovery (Ye et al., 1998) of novel anti-microtubule and anti-cancer properties of an old, orally available, non-toxic, non-sedative, non-addictive, plant derived alkaloid, noscapine, which has been used historically as an anti-cough medicine. Although noscapine and some of its analogs are generally effective in reducing tumor burden of many tumor types, it does not completely eliminate them.

Accordingly, the present inventors discovered that a folate-noscapine analog as described herein can be strategically and effectively targeted to prevent and treat aggressive, metastatic tumors, especially after first line of debulking surgery, which often leaves some tumor cells and some metastatic microfoci. This hypothesis is firmly based upon our extremely promising preliminary data. The data show the following.

(1) FR-α receptors are overexpressed in many tumor types, particularly in cancers of ovary, breast, prostate, and brain (gliomas and pituitary adenomas).

(2) Inspired by structure-function and in silico modeling and docking studies, we have been able to successfully synthesize, in a regioselective and stereoselective fashion, a noscapine-folate conjugate, Targetin, in high yield.

(3) Targetin retains MT-binding- and resulting MT dynamics attenuating-activities of the lead compound, noscapine (in fact it is ~3 fold more effective).

(4) Folate receptor overexpressing cancer cells are much more sensitive to Targetin treatment than noscapine, and free folic acid competes with Targetin indicating folate receptor-mediated augmentation of cytotoxicity of Targetin.

Example 7

Bioluminescent Reporter Imaging, Data Collection and Analyses, Specific Technical Details Mice can be anesthetized with ketamine/xylazine/acepromazine and then injected intraperitoneally with 25 mg/ml luciferin potassium salt (Xenogen Corp.) in PBS. After five minutes, light emitted from bioluminescent tumors will be detected in vivo in real time by the Xenogen IVIS™ Imaging System. Mice can be placed on the warmed stage inside the camera box and imaged on the ventral side at multiple time points. The signals can be digitized and electronically displayed as a pseudocolor overlay onto a gray scale animal image, representing the spatial distribution of photons detected from cleaved luciferin in the cancer cells expressing luciferase. Regions of interest (ROI) from the displayed images can be drawn around the tumor sites and quantified as photons/sec using the Living Image software (Xenogen Corp.). For peritoneal metastasis, an ROI can be drawn around the major bioluminescence signal. For determination of the "fold increase" above background, average background measurements can be obtained using the same ROI on a corresponding region from control mice. Data will be divided by average background measurement and normalized to signal obtained immediately after xenografting (day 0). For evaluation of tumor growth inhibition, the Student's t-test will be used to assess differences in photon emission readings between treated and control groups (P<0.05, considered significant). Ideally, all animal experimentation will be strictly in compliance with adequate protocols and the IACUC (Institutional Animal Care and Users Committee) guidelines.

The present invention is not to be limited in scope by the specific embodiments described herein. Indeed, various modifications of the invention in addition to those described will become apparent to those skilled in the art from the foregoing description and accompanying figures. Such modifications are intended to fall within the scope of the appended claims.

Various publications are cited herein, the disclosures of which are incorporated by reference in their entireties.

The invention claimed is:

1. A method for treating a cancer in a mammal having cancer cells that overexpress folate receptors, comprising administering to the mammal a therapeutically effective amount of a composition comprising a conjugate of noscapine or a noscapine analog of Formula (I) below and folic acid or a folic acid analog in an amount sufficient to at least partially inhibit growth of the tumor wherein the cancer is selected from a group consisting of ovary, breast, prostate, and brain cancers

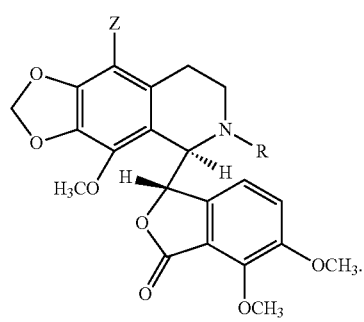

Formula I

2. The method of claim 1 wherein the mammal is a human.

3. The method of claim 1, wherein the conjugate has one of the following formulas:

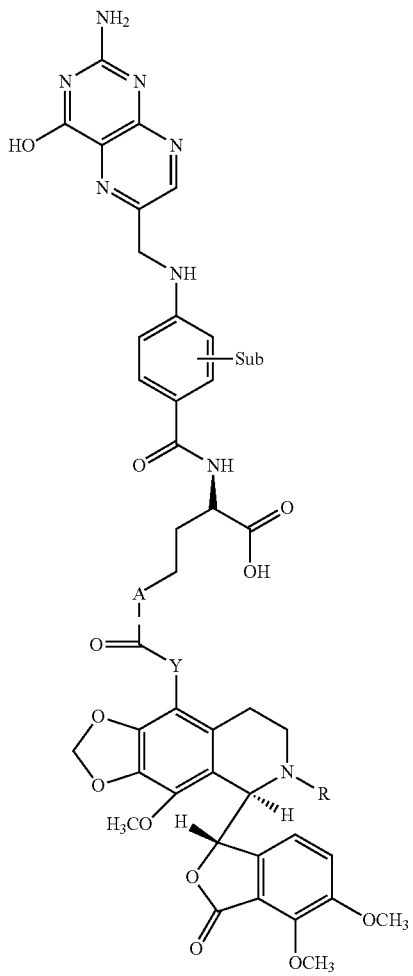

Formula 1 or salt thereof wherein:

R is H, $C_{1-6}$ alkyl, $C_{1-6}$ substituted alkyl, aryl, substituted aryl, arylalkyl, substituted arylalkyl, alkaryl, substituted alkaryl, heteroaralkyl, substituted heteroaralkyl, heterocyclyl, and substituted heterocyclyl, the term "substituted" as applied to alkyl, aryl, cycloalkyl and the like refers to the substituents selected from the group consisting of hydroxy, alkoxy, aryloxy, mercapto, aryl, heterocyclo, halo, amino, carboxyl, carbamyl, and cyano, Sub" refers to one to three substituents at any position on the aryl ring, wherein the substituents are the substituents described above, A is O, S, NR, or a covalent linkage, X is O, S, or NR, and Y is O, S, or NR;

Formula 2
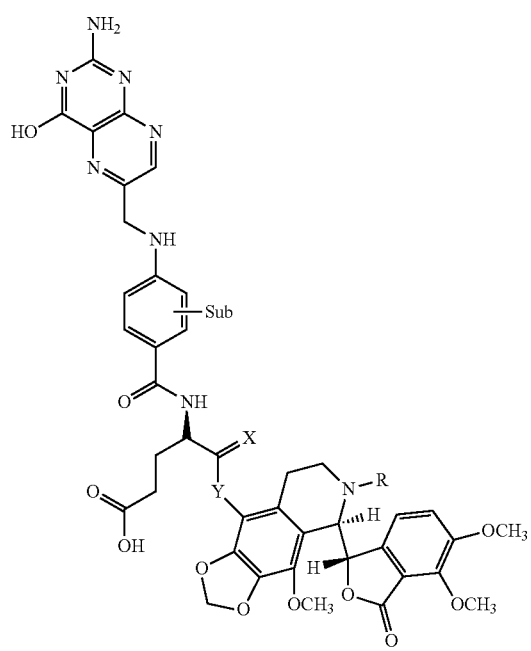
or salt thereof wherein X, Y, R, and Sub are as described above with respect to Formula 1,
Formula 3
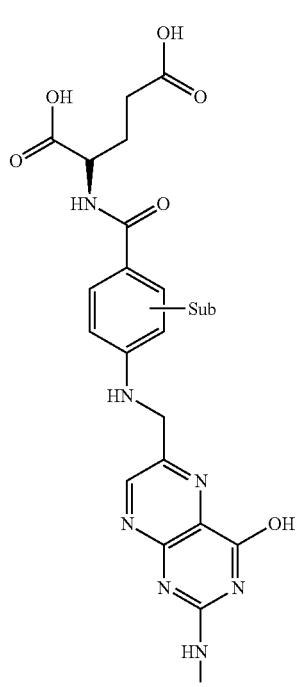
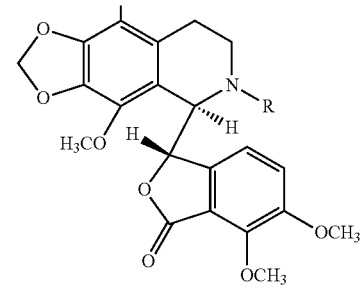
wherein or salt thereof R and Sub are as defined above with respect to Formula 1, and
Formula 4
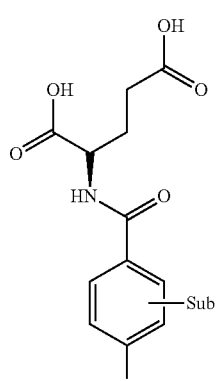
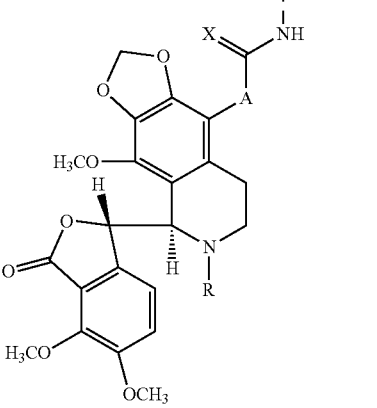
or salt thereof wherein: A, R, Sub, and X are as defined above with respect to Formula 1.

4. The method of claim 3, wherein the conjugate has the following formula:

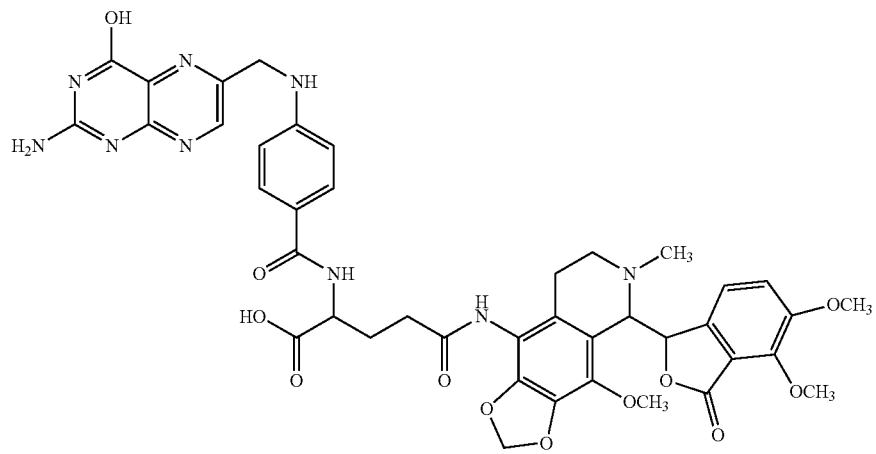 [SMILES: COc1ccc2c(c1OC)C(=O)OC2C1c2c(c(NC(=O)CCC(NC(=O)c3ccc(NCc4cnc5nc(N)nc(O)c5n4)cc3)C(=O)O)c3c(c2OC)OCO3)CCN1C]

or salt thereof.

5. A method for diagnosing the presence of tumor cells, comprising the steps of: a) administering to a patient suspected of having FR-alpha positive cancer cells a composition comprising a radiolabeled conjugate of noscapine or a noscapine analog of Formula (I) below and folic acid or a folic acid analog in an amount sufficient to bind to, and attach a radiolabel to, a tumor, and performing a diagnostic step that detects the radiolabel wherein the cancer is selected from a group consisting of ovary, breast, prostate, and brain cancers Formula I

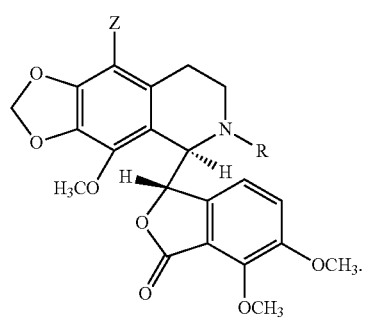

6. The method of claim 5, wherein the conjugate of noscapine or a noscapine analog and folic acid or a folic acid analog is chelated to $^{m99}$Tc in its folate moiety.

7. The method of claim 6, further comprising treating those patients diagnosed as having FR-alpha positive cancer cells with anti-cancer therapies selective for this type of cancer wherein the cancer is selected from a group consisting of ovary, breast, prostate, and brain cancers.

8. A compound having one of the following formulas:

Formula 1

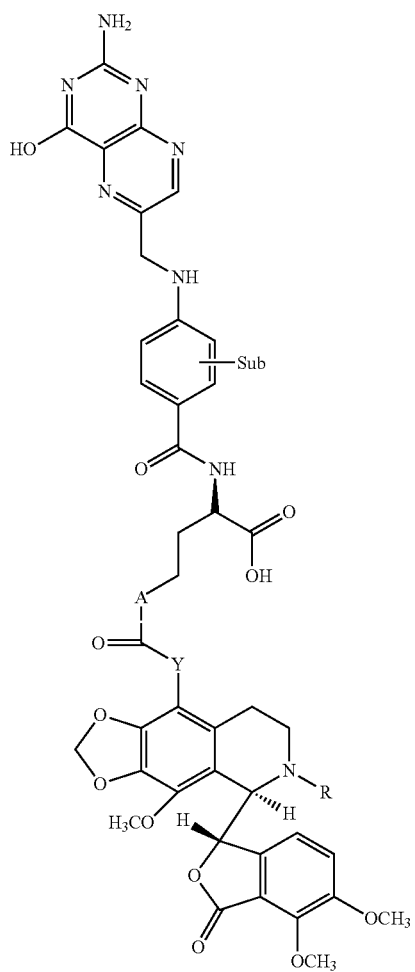

or salt thereof wherein:

R is H, $C_{1-6}$ alkyl, $C_{1-6}$ substituted alkyl, aryl, substituted aryl, arylalkyl, substituted arylalkyl, alkaryl, substituted alkaryl, heteroaralkyl, substituted heteroaralkyl, heterocyclyl, and substituted heterocyclyl, the term "substituted" as applied to alkyl, aryl, cycloalkyl and the like refers to the substituents selected from the group consisting of hydroxy, alkoxy, aryloxy, mercapto, aryl, heterocyclo, halo, amino, carboxyl, carbamyl, and cyano, Sub" refers to one to three substituents at any position on the aryl ring, wherein the substituents are the substituents described above, A is O, S, NR, or a covalent linkage, X is O, S, or NR, and Y is O, S, or NR;

Formula 2

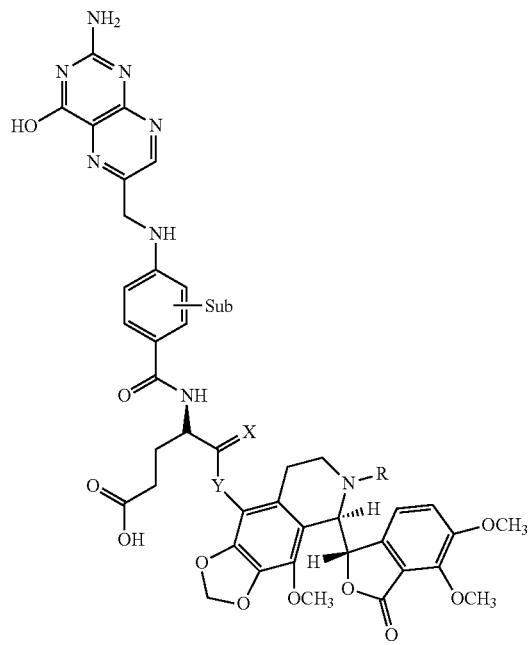

or salt thereof wherein X, Y, R, and Sub are as described above with respect to Formula 1, Formula 3

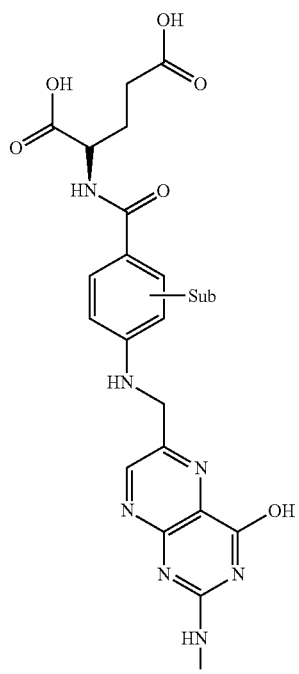

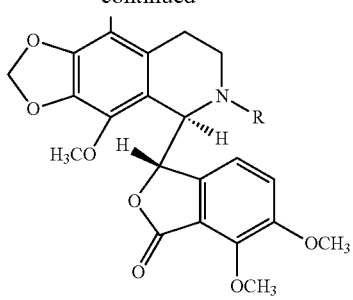

or salt thereof wherein R and Sub are as defined above with respect to Formula 1, and Formula 4

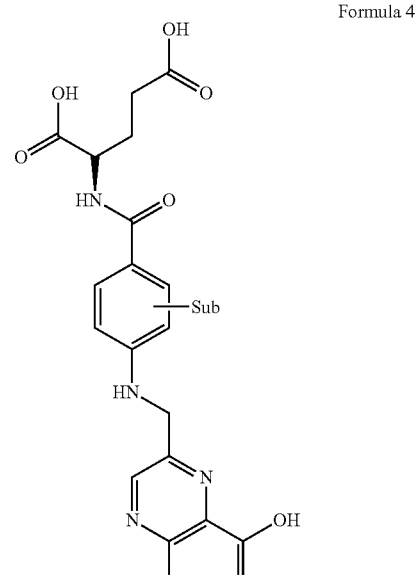

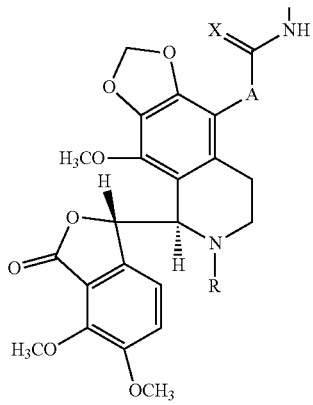

or salt thereof wherein: A, R, Sub, and X are as defined above with respect to Formula 1.

9. The compound of claim 8, wherein the compound has the following formula:

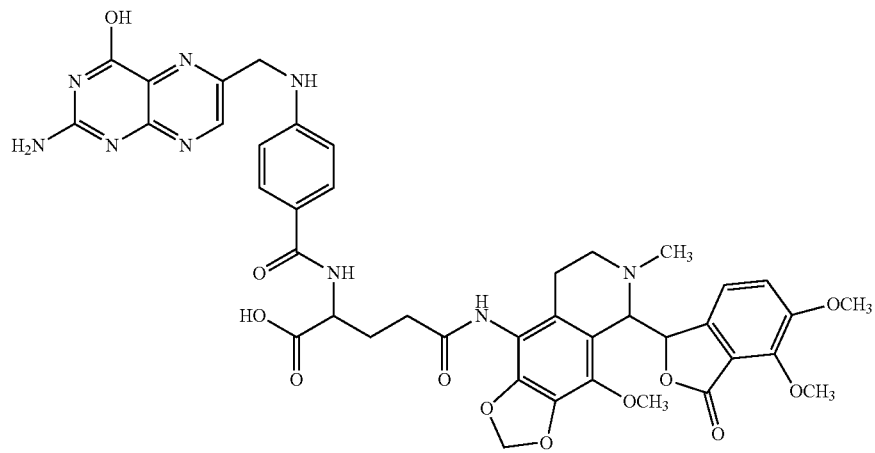 [SMILES: COc1ccc2c(c1OC)C(=O)OC2C1c2c(c(NC(=O)CCC(NC(=O)c3ccc(NCc4cnc5nc(N)nc(O)c5n4)cc3)C(=O)O)c3c(c2OC)OCO3)CCN1C]
or salt thereof.
* * * * *

UNITED STATES PATENT AND TRADEMARK OFFICE
CERTIFICATE OF CORRECTION

PATENT NO. : 8,426,398 B2 Page 1 of 1
APPLICATION NO. : 13/142908
DATED : April 23, 2013
INVENTOR(S) : Joshi et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 104 days.

Signed and Sealed this
Eighth Day of September, 2015

Michelle K. Lee
*Director of the United States Patent and Trademark Office*